United States Patent [19]

Kita et al.

[11] Patent Number: 5,492,798
[45] Date of Patent: Feb. 20, 1996

[54] SILVER HALIDE COLOR PHOTOGRAPHIC LIGHT-SENSITIVE MATERIAL

[75] Inventors: Hiroshi Kita; Hiroshi Ishidai, both of Tokyo, Japan

[73] Assignee: Konica Corporation, Tokyo, Japan

[21] Appl. No.: 352,775

[22] Filed: Dec. 1, 1994

[30] Foreign Application Priority Data

Dec. 1, 1993 [JP] Japan .................................. 5-301944

[51] Int. Cl.⁶ .................................................. G03C 7/38
[52] U.S. Cl. ...................................................... 430/558
[58] Field of Search ............................................. 430/558

[56] References Cited

U.S. PATENT DOCUMENTS

| | | | |
|---|---|---|---|
| 2,600,788 | 6/1952 | Loria et al. | 430/386 |
| 2,807,653 | 9/1957 | Fibey et al. | 568/727 |
| 3,519,429 | 7/1970 | Lestina | 430/551 |
| 3,725,067 | 4/1973 | Bailey et al. | 430/558 |
| 3,758,309 | 9/1973 | Bailey et al. | 430/587 |
| 3,810,761 | 5/1974 | Bailey et al. | 430/522 |
| 5,254,451 | 10/1993 | Kita et al. | 4303/558 |

FOREIGN PATENT DOCUMENTS

| | | |
|---|---|---|
| 0285274 | 10/1988 | European Pat. Off. ............... 430/558 |
| 241289 | 9/1993 | Japan . |
| 5-241292 | 9/1993 | Japan . |
| 5-241283 | 9/1993 | Japan . |

*Primary Examiner*—Lee C. Wright
*Attorney, Agent, or Firm*—Finnegan, Henderson, Farabow, Garrett & Dunner

[57] ABSTRACT

Disclosed is a silver halide color photographic light-sensitive material comprising a magenta coupler represented by Formulas I or II:

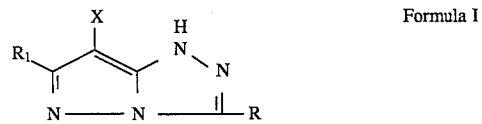

Formula I

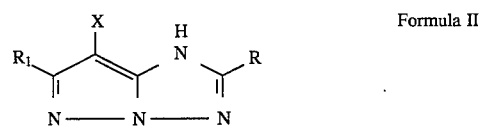

Formula II wherein $R_1$ represents a substituent; X represents a hydrogen atom or a group capable of splitting off upon reaction with an oxidized product of a color developing agent; and R represents a substituted alkyl group containing at least two units represented by Formula III:

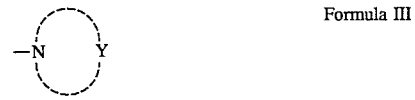

Formula III wherein Y represents a non-metallic atomic group necessary to form a 5-membered or 6-membered heterocyclic ring together with a nitrogen atom.

9 Claims, No Drawings

SILVER HALIDE COLOR PHOTOGRAPHIC LIGHT-SENSITIVE MATERIAL

FIELD OF THE INVENTION

This invention relates to a silver halide color photographic light sensitive material containing a magenta coupler and, particularly, to a silver halide color photographic light sensitive material in which a color reproducibility and color producibility can be excellent and a dye image stable against heat and light can be obtained when containing a novel pyrazoloazole type magenta coupler therein.

BACKGROUND OF THE INVENTION

As for the couplers generally applicable to silver halide color photographic light sensitive materials, there have been known couplers including, for example, the yellow couplers each comprising a open-chained ketomethylene type compound, the magenta couplers each comprising a pyrazolone or pyrazoloazole type compound and the cyan couplers each comprising a phenol or naphthol type compound. Among them, a 5-pyrazolone compound has very often been used for the magenta couplers so far.

The known pyrazolone magenta couplers are described in, for example, U.S. Pat. Nos. 2,600,788 and 3,519,429 and Japanese Patent Publication Open to Public Inspection (hereinafter referred to as JP OPI Publication) Nos. 49-111631(1974) and 57-35858(1982). However, the dyes made of the pyrazolone magenta couplers have produced an undesirable side-absorption which has been demanded for the improvements, as described in 'The Theory of the Photographic Process', the 4th Ed., Macmillan Publishing Co., 1977, pp.356–358; 'Fine Chemical', Vol. 14, No. 8, CMC Press, pp. 38–41; and the Lecture Transcription published at the 1985 Annual Convention of the Society of Photographic Science of Japan, pp. 108–110.

As described in the above-given literatures, the dyes made of the pyrazoloazole type magenta couplers do not produce any side-absorption. The above-given literatures, U.S. Pat. Nos. 3,725,067, 3,758,309 and 3,810,761 and so forth describe that the couplers of this type are excellent.

However, the light-fastness of azomethine dyes made of the couplers are so seriously low that the characteristics of color photographic light sensitive materials, particularly those of print type color photographic light sensitive materials are seriously spoiled.

The studies and researches have been tried for improving the light-fastness. For example, JP OPI Publication Nos. 59-125732(1984), 61-282845(1986), 61-292639(1986) and 61-279855(1986) disclose the techniques of making combination use of a pyrazoloazole type coupler and a phenol type compound or a phenylether compound and JP OPI Publication Nos. 61-72246(1986), 62-208048(1987), 62-157031(1987) and 63-163351(1988) disclose the techniques of making combination use of a pyrazoloazole type coupler and an amine type compound.

Further, JP OPI Publication No. 63-24256(1988) proposes for a pyrazoloazole type magenta coupler having an alkyloxyphenyloxy group.

In the above-given techniques, the light-fastness of magenta dye images are still unsatisfactory and the improvements thereof have been eagerly demanded.

SUMMARY OF THE INVENTION

This invention has been made for solving the above-mentioned problems. It is, therefore, an object of the invention is to provide a silver halide color photographic light sensitive material excellent in color reproducibility and color developability and remarkably improved in light-fastness of magenta dye images.

The above-mentioned objects are attained by either of the following items ① through ④.

① A silver halide color photographic light-sensitive material containing a magenta coupler represented by the following Formula [I] or [II]:

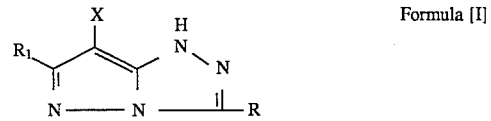

Formula [I]

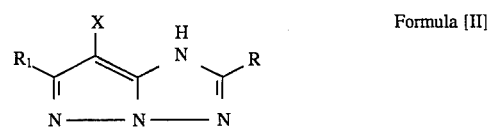

Formula [II]

wherein $R_1$ represents a substituent; X represents a hydrogen atom or a group capable of splitting off upon reaction with an oxidized product of a color developing agent; and R represents a substituted alkyl group containing at least two substituents represented by Formula [III]:

Formula [III]

wherein Y represents a non-metallic atomic group necessary to form a 5-membered or 6-membered hetero cyclic ring together with a nitrogen atom.

② A silver halide color photographic light-sensitive material wherein, in a magenta coupler represented by Formula [I] or [II], a substituent represented by R is a substituted alkyl group containing at least two substituents represented by Formula[IV]:

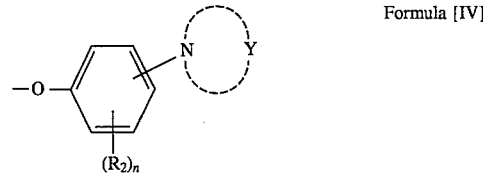

Formula [IV]

wherein $R_2$ represents a substituent; n represents an integer of 0 to 4; and Y represents a non-metallic atomic group necessary to form a 5-membered or 6-membered heterocyclic ring together with a nitrogen atom.

③ A silver halide color photographic light-sensitive material wherein a magenta coupler represented by Formula [I] or [II] is represented by the following Formula [I-a] or [II-a]:

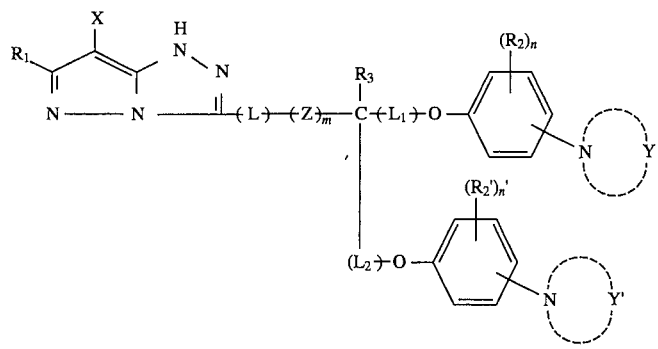

Formula [I-a]

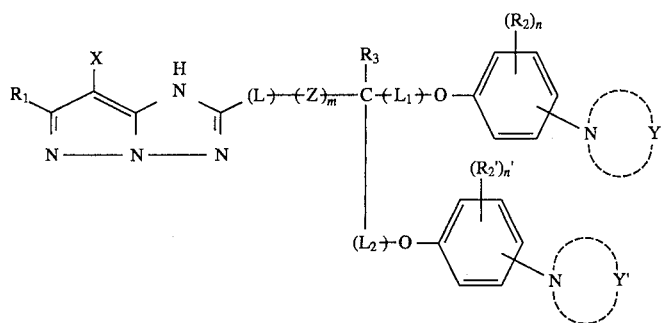

Formula [II-a]

wherein $R_1$ represents a substituent; X represents a hydrogen atom or a group capable of splitting off upon reaction with an oxidized product of a color developing agent; $R_2$ and $R_2'$ represents a substituent; $R_3$ represents a hydrogen atom or a substituent; L represents a single linkage or a divalent linkage group; Z represents

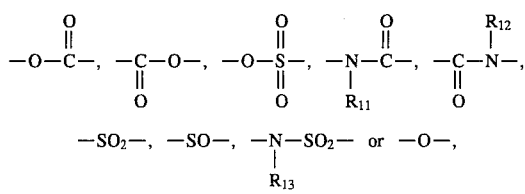

m represents 0 or 1; $R_{11}$, $R_{12}$ and $R_{13}$ each represent a hydrogen atom or a substituent; $L_1$ and $L_2$ represent a divalent linkage group; n and n' each represent an integer of 0 to 4; Y and Y' each represent a non-metallic atomic group necessary to form a 5-membered or 6-membered heterocyclic ring together with a nitrogen atom, provided that m represents 0 when L represents a single linkage.

④ A silver halide color photographic light-sensitive material wherein a magenta coupler represented by Formula [I] or [II] is represented by the following Formula [I-b] or [II-b]:

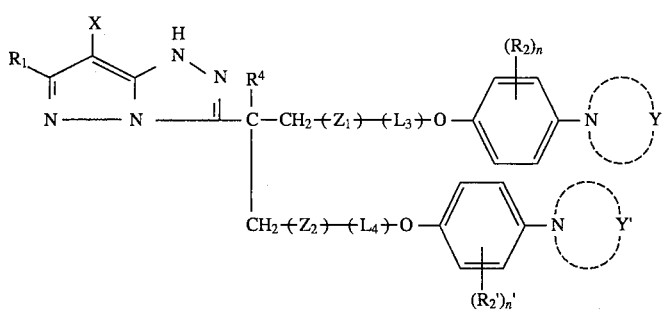

Formula [I-b]

-continued

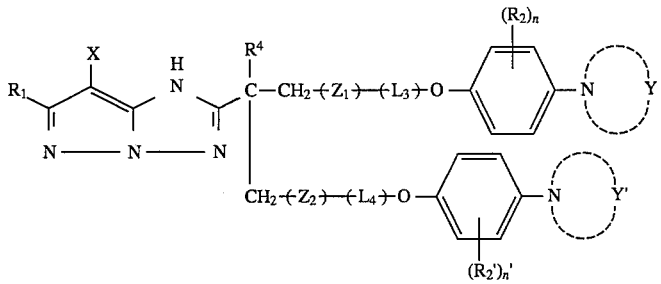

Formula [II-b]

wherein $R_1$ represents a substituent; X represents a hydrogen atom or a group capable of splitting off upon reaction with an oxidized product of a color developing agent; $R_2$ and $R_2'$ each represent a substituent; $R_4$ represents a hydrogen atom, an alkyl group or a substituted alkyl group; $Z_1$ and $Z_2$ each represent

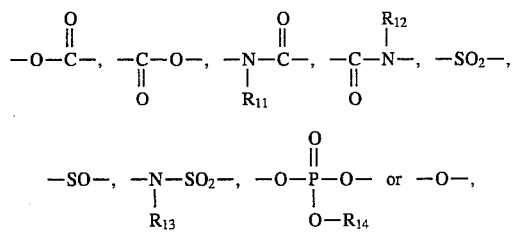

$R_{11}$, $R_{12}$, $R_{13}$ and $R_{14}$ each represent a hydrogen atom or a substituent; $L_3$ and $L_4$ each represent an alkylene group; n and n' represent an integer of 0 to 4; Y and Y' each represent an non-metallic atomic group necessary to form a 5-membered or 6-membered heterocyclic ring together with a nitrogen atom.

Hereinafter, the present invention will be described in detail.

In the above-mentioned Formulas [I], [II], [II-a], [I-b] and [II-b], there is no specific limitation, as a substituent, to $R_1$, $R_2$, $R_2'$, $R_3$, $R_{11}$, $R_{12}$, $R_{13}$ and $R_{14}$ (hereinafter, referred to as $R_1$ through $R_{14}$). However, typically, an alkyl group, an aryl group, an anilino group, an acylamino group, a sulfonamide group, an alkylthio group, an aryl thio group, an alkenyl group and a cycloalkyl group are cited. In addition, a halogen atom, a cycloalkenyl group, an alkinyl group, a heterocycle, a sulfonyl group, a sulfinyl group, a phosphonyl group, an acyl group, a carbamoyl group, a sulfamoyl group, a cyano group, an alkoxy group, an aryloxy group, a heterocyclicoxy group, a siloxy group, an acyloxy group, a carbamoyloxy group, an amino group, an alkylamino group, an imide group, an ureido group, a sulfamoylamino group, an alkoxycarbonylamino group, an aryloxycarbonylamino group, an alkoxycarbonyl group, an aryloxycarbonyl group, a carboxy group, a hydroxy group and a heterocyclic thio group and a spiro compound residual group and a hydrogen carbon compound residual group having a bridge-head atom, are cited.

Alkyl groups represented by $R_1$ through $R_{14}$ preferably include those having 1 to 32 carbons. They may be straight-chained or branch-chained.

Aryl groups represented by $R_1$ through $R_{14}$ preferably include a phenyl group. An acylamino group represented by $R_1$ through $R_{14}$ includes an alkylcarbonylamino group and an arylcarbonylamino group.

Sulfonamide group represented by $R_1$ through $R_{14}$ include an alkylsulfonylamino group and an arylsulfonylamino group.

An alkyl component and an aryl component respectively in the alkylthio group and the arylthio group represented by $R_1$ through $R_{14}$ include the alkyl group and the aryl group represented by the above-mentioned $R_1$ through $R_{14}$.

The alkenyl group represented by $R_1$ through $R_{14}$ include preferably, those having 2 to 32 carbons. The cycloalkyl group represented thereby include preferably, those having 3 to 12 carbons, and more preferably those having 5 to 7 carbons. The alkenyl group may be straight-chained or branched.

The cycloalkenyl group represented by $R_1$ through $R_{14}$ include preferably, those having 3 to 12 carbons, and more preferably those having 5 to 7 carbons.

The sulfonyl group represented by $R_1$ through $R_{14}$ include, an alkylsulfonyl group and an arylsulfonyl group;

The sulfinyl group represented thereby include, for example, an alkylsulfinyl group, and an arylsulfinyl group;

The phosphonyl group represented thereby include, for example, an alkylphosphonyl group, an alkoxyphosphonyl group, an aryloxyphosphonyl group and an arylphosphonyl group;

The acyl group represented thereby include, for example, an alkylcarbonyl group and an arylcarbonyl group;

The carbamoyl group represented thereby include, for example, an alkylcarbamoyl group and an aryl carbamoyl group;

The sulfamoyl group represented thereby include, for example, an atkylsulfamoyl group and an arylsulfamoyl group;

The acyloxy group represented thereby include, for example, an alkylcarbonyloxy group and an arylcarbonyloxy group;

The carbamoyloxy group represented thereby include, for example, an alkylcarbamoyloxy group and an arylcarbamoyloxy group;

The ureido group represented thereby include, for example, an alkylureido group and an arylureido group;

The sulfamoylamino group represented thereby include, for example, an alkylsulfamoylamino group and an arylsulfamoylamino group;

The heterocyclic ring represented thereby include, for example, preferably, those having a 5-membered to 7-membered group, practically including a 2-furyl group, a 2-thienyl group, a 2-pyrymidynyl group and a 2-benzothiazolyl group;

The siloxy group represented thereby include, for example, a trimethylsiloxy group, a triethylsiloxy group and a dimethylbutylsiloxy group;

The imido group represented thereby include, for example, a succinic acid imido group, a 3-heptadecylsuccinic acid imido group, a phthalic acid imido group and a glutarimido group;

The spiro compound residual group represented thereby include, for example, a spiro[3,3]heptane-1-yl; and The hydrogen carbon residual group having a bridge-head atom, represented thereby include, for example, a bicyclo [2.2.1]heptane-1-yl group, a tricyclo[3.3.1.1$^{37}$]decane-1-yl, 7,7-dimethyl-bicyclo[2.2.1]heptane-1-yl.

Each group represented by $R_1$ through $R_{14}$, in addition, includes those having a substituent.

Among substituents represented by $R_1$, the preferable are an alkyl group, an alkoxy group, an aryloxy group, an anilino group, an acylamino group and a ureido group. The especially preferable are an alkyl group, an alkoxy group and an aryloxy group. The most preferable is an alkyl group.

The groups capable of splitting off upon reaction with an oxidized product of a color developing agent represented by X includes a halogen atom (for example, a chlorine atom, a bromine atom and a fluorine atom), an alkoxy group, an aryloxy group, a heterocyclicoxy, an acyloxy group, a sulfonyloxy group, an alkoxycarbonyloxy group, an aryloxycarbonyl group, an alkyloxalyloxy group, an alkoxyoxalyloxy group, an alkylthio group, an arylthio group, a heterocyclicthio group, an alkyloxythiocarbonylthio group, an acylamino group, a sulfonamido group, nitrogen-containing heterocyclic ring bonded with an nitrogen atom, an alkyloxycarbonylamino group, an aryloxycarbonylamino group and a carboxyl group. Among them, halogen atoms including, particularly, a chlorine atom are preferable.

When n and n' represent 2 or more, a plurality of $R_2$ and $R_2'$ may be the same or the different, and a plurality of $R_2$ and $R_2'$ are also allowed to form a condensed ring in this case.

In addition, oligomeric couplers such as a dimeric couplers containing a pyrazolotrizole ring in $R_1$, R or X and polymeric couplers are included in the present invention.

In the above-mentioned Formulas [I-a], [II-a], [I-b] and [II-b], a divalent linkage group represented by L, $L_1$ and $L_2$ include a divalent group induced from an alkyl group, an aryl group, an anilino group, an acylamino group, a sulfonamido group, an alkylthio group, an arylthio group, an alkenyl group, a cycloalkyl group, a cycloalkenyl group, an alkinyl group, a heterocycle, a sulfonyl group, a sulfinyl group, a phosphonyl group, an acyl group, a carbamoyl group, a sulfamoyl group, an alkoxy group, an aryloxy group, a heterocyclicoxy group, an acyloxy group, a carbamoyloxy group, an amino group, an alkylamino group, an imido group, an ureido group, a sulfamoylamino group, an alkoxycarbonylamino group, an aryloxycarbonylamino group, an alkoxycarbonyl group, an aryloxycarbonyl group, a carboxy group a hydroxy group and a heterocyclicthio group and a divalent group capable of being formed by combining these divalent groups.

In Formula [I-b] and [II-b], an alkylene group represented by $L_3$ and $L_4$ include a straight-chained or branched alkylene groups each having 1 to 18 carbons (for example, a methylene group, an ethylene group, a 1-methylethylene group, a decylmethylene group and 1,1-dimethylpropylene group).

In Formulas [I-b] and [II-b], an alkyl group represented by $R_4$, which may be straight-chained or branched, is preferably that having 1 to 32 carbons. A substituent of a substituted alkyl group represented by $R_4$ is the same as a substituent represented by the above-mentioned $R_1$ through $R_{14}$.

In Formulas [I-a], [II-a], [I-b] and [II-b], it is preferable that Y and Y', n and n', $R_2$ and R' each represent the same.

In Formulas [I], [II], [I-a], [II-a], [I-b] and [II-b], a non-metallic atomic group represented by Y and Y' include preferably the following group.

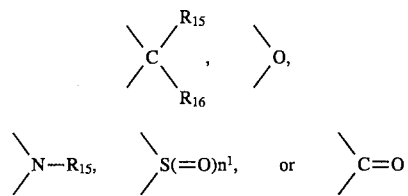

Further, it is more preferable that the non-metal atomic group represented by Y and Y' include >O group or >S(=O)$_2$ group.
wherein $R_{15}$ and $R_{16}$ each represent a hydrogen atom, an alkyl group or an aryl group; and $n^1$ is an integer of 0 to 2.

In the foregoing Formulas [I], [II], [I-a], [II-a], [I-b] and [II-b], the 5-membered to 6-membered heterocyclic rings represented by

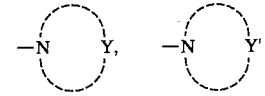

may be saturated or unsaturated. However, they cannot be 6π, 10π or 14π type aromatic heterocyclic rings. They are preferable to be saturated rings.

These heterocyclic rings are each allowed to have a substituent represented by $R_1$ through $R_{14}$.

Hereunder, the typical examples of the magenta coupler relating to the present invention will be given. However, the present invention shall not be limited thereto.

M-1

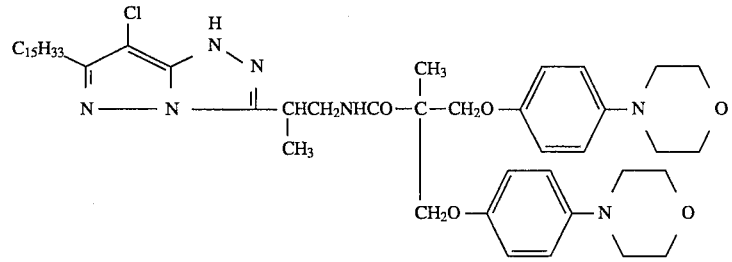

-continued
M-2
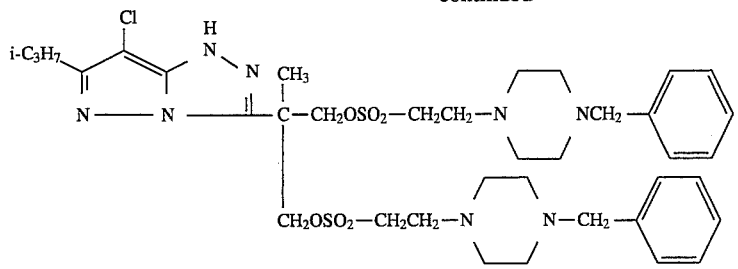
M-3
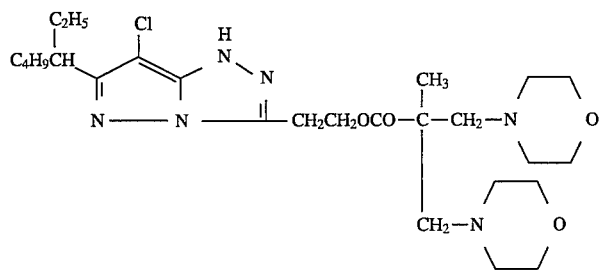
M-4
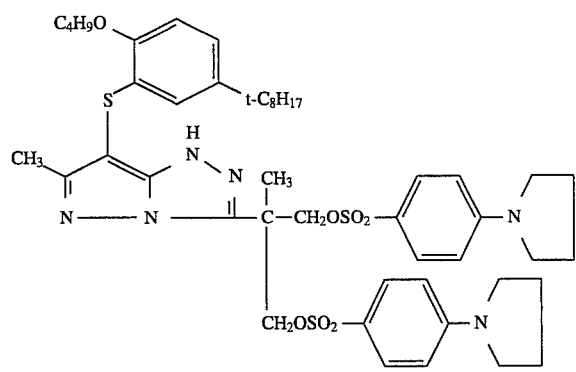
M-5
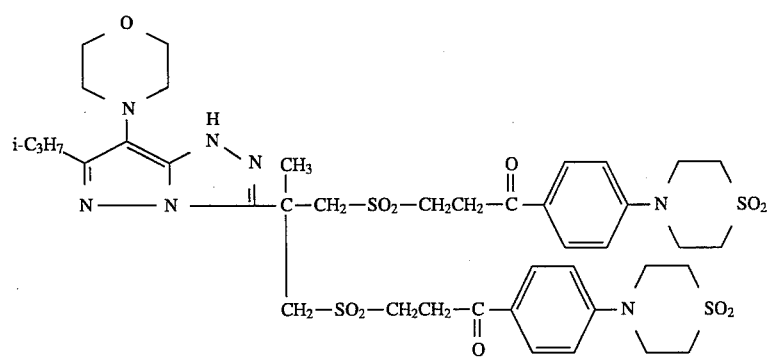
M-6
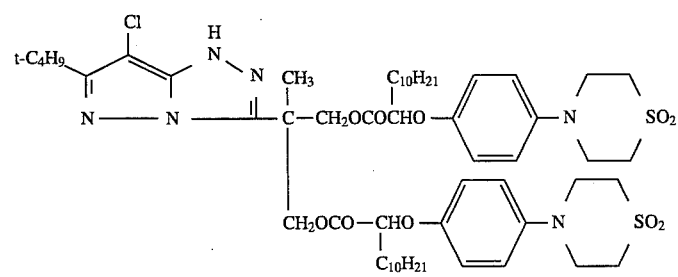

-continued
M-7
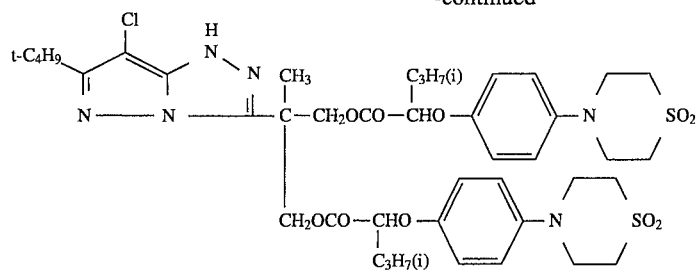
M-8
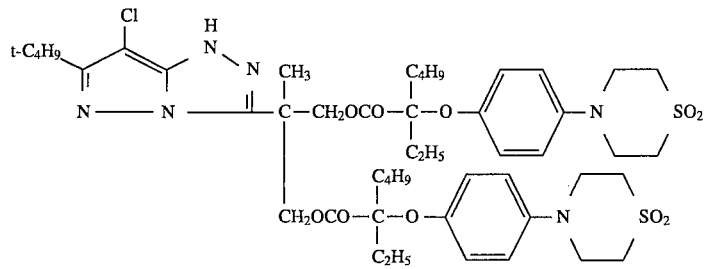
M-9
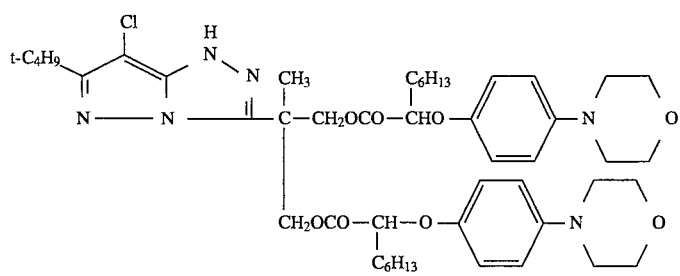
M-10
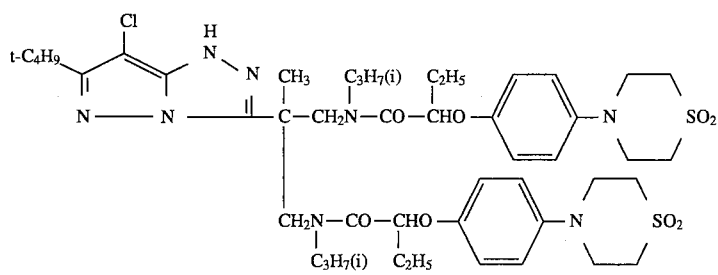
M-11
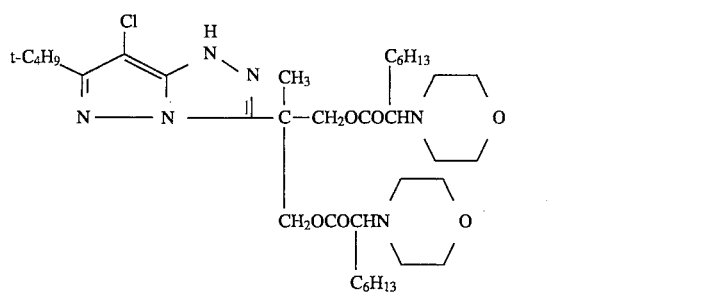
M-12
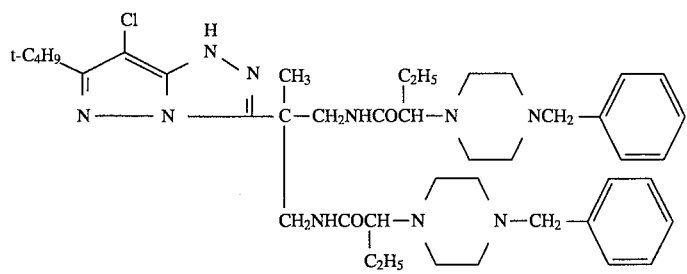

-continued
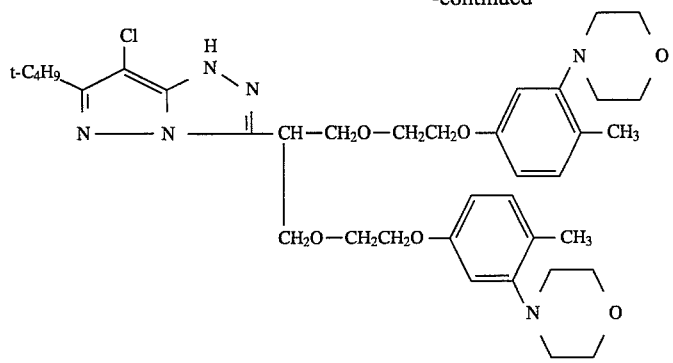
M-13
M-14
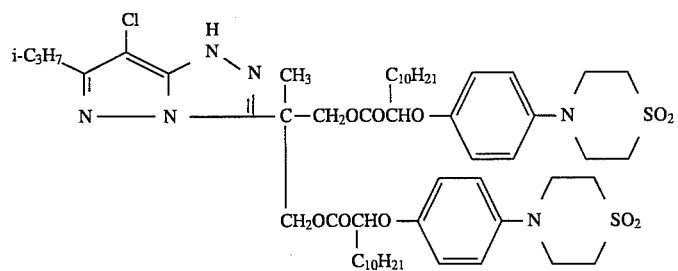
M-15
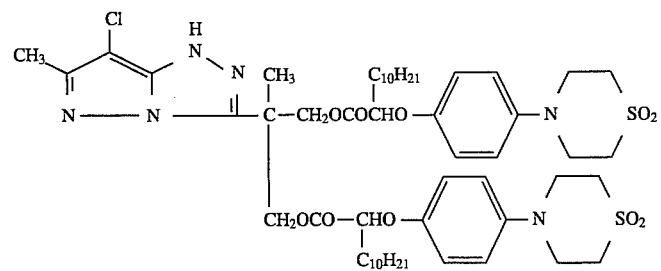
M-16
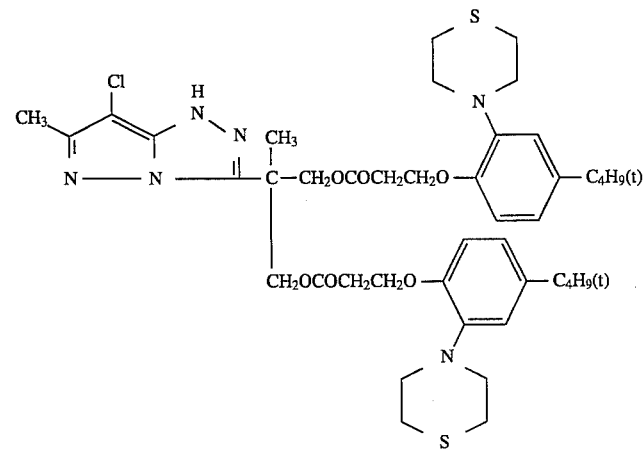
M-17

-continued
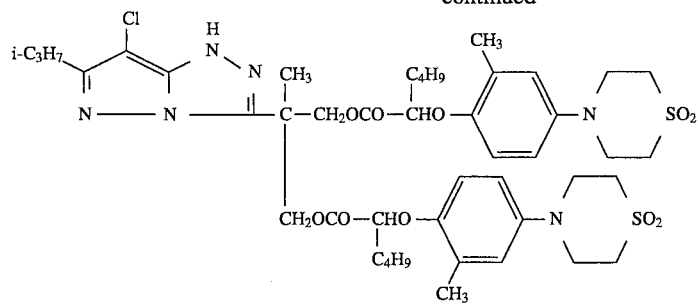
M-18
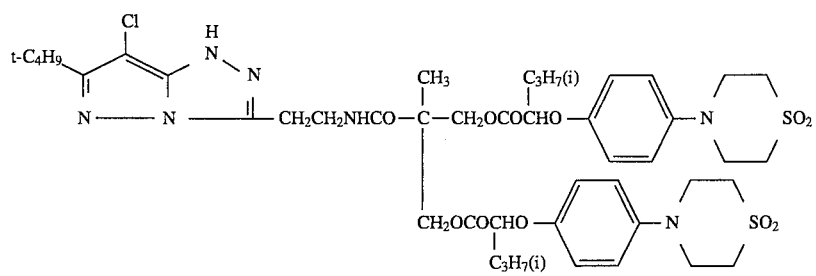
M-19
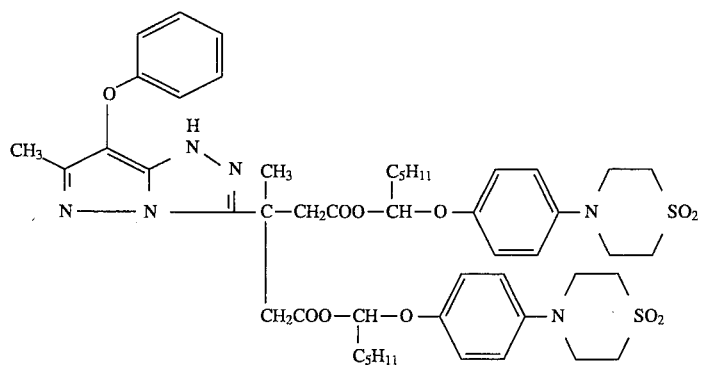
M-20
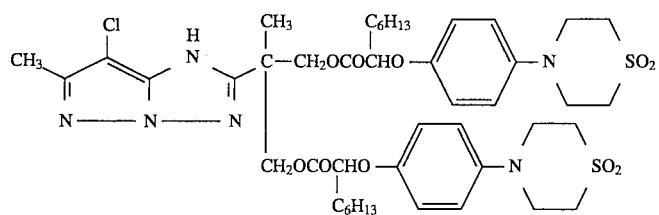
M-21
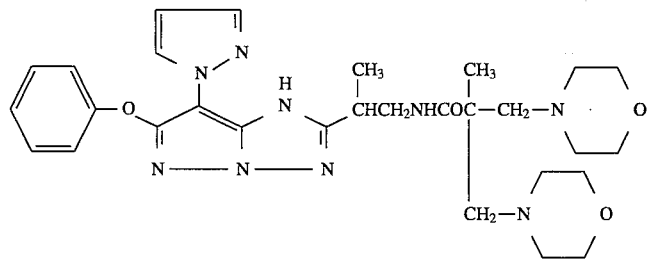
M-22
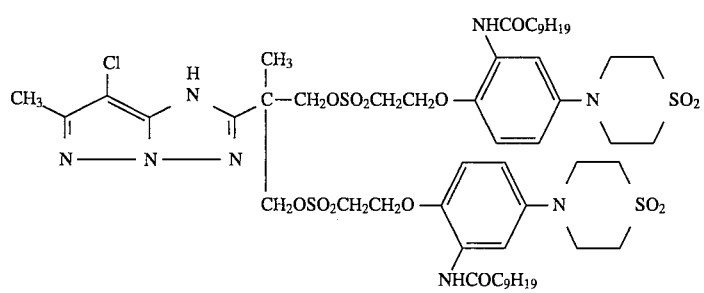
M-23

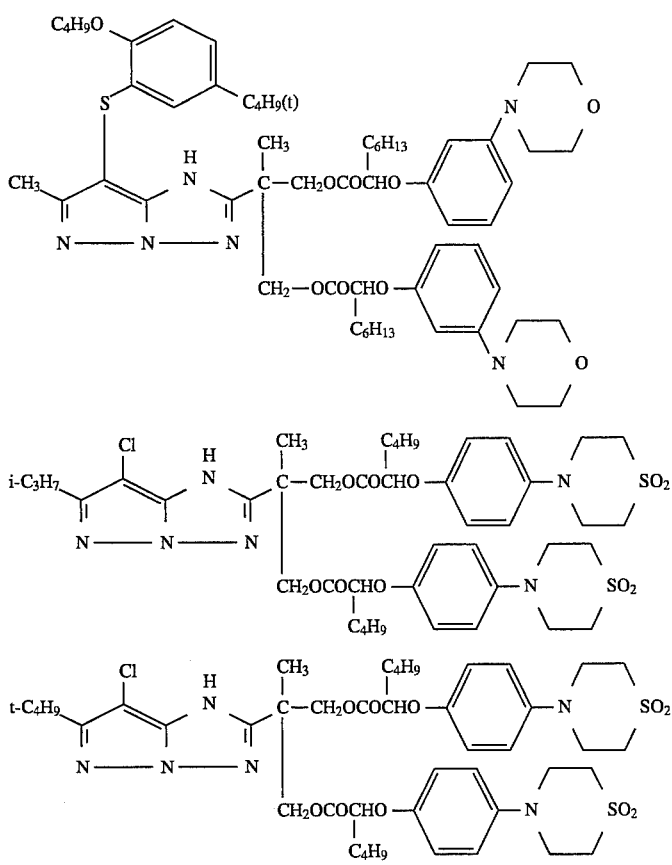

The above-mentioned pyrazoloazole type magenta couplers relating to the invention can readily be synthesized by the skilled in the art with reference to 'Journal of the Chemical Society', Perkin I, 1977, pp. 2047–2052; U.S. Pat. No. 3,725,067; JP OPI Publication Nos. 59-99437(1984), 58-( 42045(1983), 59-162548 (1984), 59-171956(1984), 60-33552(1985), 60-43659(1985), 60-172982(1985), 60-190779(1985), 61- 189539(1986), 61-241754(1986), 63-163351(1988) and 62- 157031(1987).

The typical synthesizing examples of the above-mentioned pyrazoloazole type magenta couplers relating to the invention will now be given below.

Synthesis Example

<Synthesis of Exemplified Compound M-6>

The synthesis procedures thereof will be given below.

Synthesis procedures

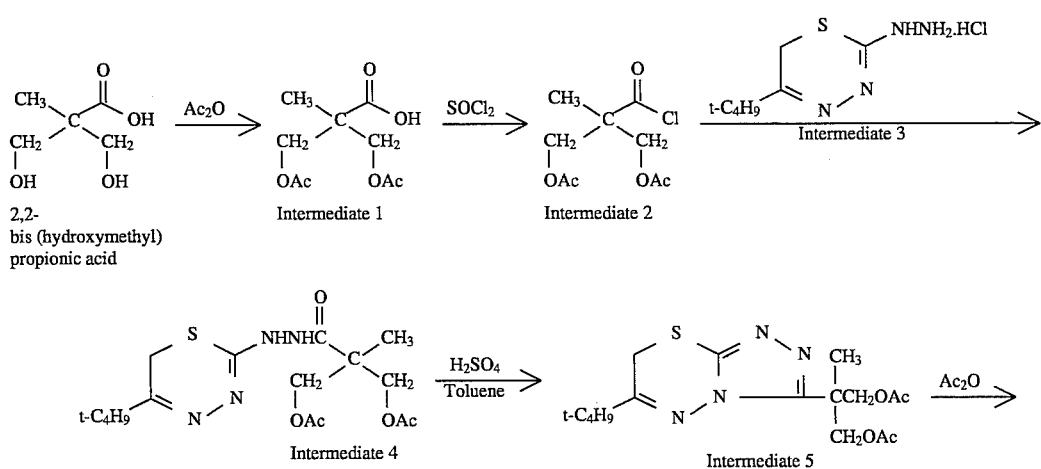

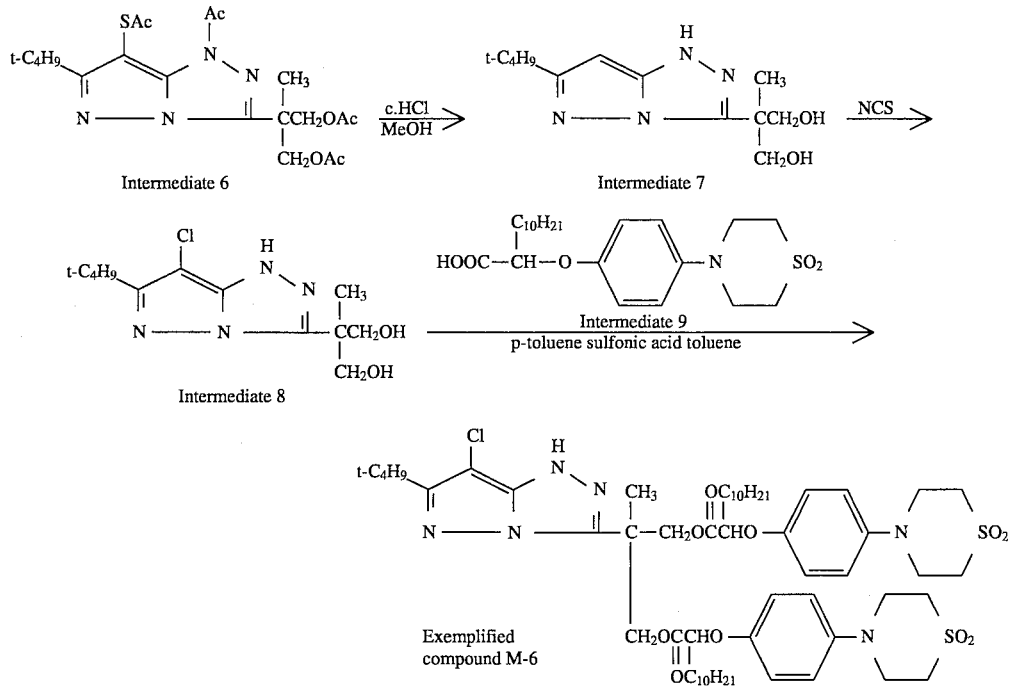

Synthesis of Intermediate 1

To 40.2 g of 2,2-bis(hydroxymethyl)propionic acid, 120 ml of acetic acid anhydride was added and heated and stirred at 70° C. for 2 hours. The resulting solution was poured into 100 ml of 0.6N hydrochloric acid with 100 g of ice. After stirring for 1 hour, the solution was extracted with 300 ml of ethyl acetate. The resulting organic phase was washed twice with 100 ml of water. After that, the resulting solution was dried with anhydrous magnesium sulfate. The solvent was then distilled off under reduced pressure. The resulting oily product was recrystalized with water. Thus, 47.4 g of white crystallized intermediate 1 was obtained. (The structure thereof was confirmed by $^1$H-NMR, FD mass-spectral analysis and IR spectral analysis.)

Synthesis of Intermediate 5

To 47.4 g of intermediate 1, 200 ml of toluene and 47 ml of thionyl chloride were added. The resulting solution was subjected to heating and refluxing for 4 hours. Following that, toluene and excessive thionyl chloride were removed, Thus, 51.4 g of brown oily intermediate 2 was obtained.

Next, to 43.5 g of intermediate 3, 450 ml of acetonitrile and 51.4 g of intermediate 2 were added. The resulting solution was heated and refluxed for 3 hours. Following that, the mixture was cooled to room temperature. After the solvent was distilled off under reduced pressure, 400 ml of toluene and 6 ml of concentrated sulfuric acid was added to the resulting oily-substance. The mixture was heated and refluxed for 2 hours. The resulting solution was cooled to room temperature. To the solution, 500 ml of ethyl acetate was added. In addition, to this solution, a sodium hydrogen carbonate aqueous solution was added until the water phase shows weak basicity. After that, the solution was divided. The resulting organic phase was washed, and dried with anhydrous magnesium sulfate. Then, the solvent was distilled off under reduced pressure. Following that, the mixture was refined in silica gel chromatography, so that, 54.6 g of slight yellowish oily intermediate 5 was obtained. (The structure thereof was confirmed by $^1$H-NMR, FD mass-spectral analysis and IR spectral analysis.)

Synthesis of Intermediate 7

To 54.6 g of intermediate 5, 300 ml of acetic acid anhydride was added, and then, the mixture was heated and refluxed for 3 hours. Following that, excessive acetic acid anhydride was removed under normal pressure. Next, 200 ml of methanol was added to the reaction products. Then, 60 ml of concentrated hydrochloric acid was dropped. Then, the resulting mixture was heated and refluxed for 3 hours. After reaction, the resulting solution was cooled to room temperature. Crystallized sulfur was filtrated. Then, it was left for one night. The resulting precipitated crystals were filtered (46 g), and, to these crystals, 1000 ml of ethyl acetate and 80 ml of a saturated sodium hydrogen carbonate aqueous solution were added. The mixture was heated and stirred for one hour. Then, the solution was divided, and the resulting organic phase was dried, and the solvent was distilled off under reduced pressure. After that, the resulting product was recrystalized with a mixed solvent of ethyl acetate and hexane. Thus, 38.3 g of white crystallized intermediate 7 was obtained. (The structure thereof was confirmed by $^1$H-NMR, FD mass-spectral analysis and IR spectral analysis.)

Synthesis of Exemplified Compound M-6

In 300 ml of tetrahydrofuran, 38.3 g of intermediate 7 was dissolved. After that, the resulting solution was cooled with ice. The temperature of the solution was controlled to 5° C. To this solution, 15.2 g of N-chlorosuccinic imide was added gradually in a state of solid. The mixture was stirred at 5° to 7° C. for 2 hours. After the solvent was distilled off under reduced pressure, and 700 ml of ethyl acetate and 150 ml of water were added thereto. The resulting solution was divided. Following that, organic phase was dried and ethyl acetate was distilled off under reduced pressure. The resulting product was recrystalized with a mixed solvent of ethyl acetate and hexane. Thus, 41.9 g of intermediate 8 was obtained.

To 15.1 g of the resulting intermediate 8, 49.2 g of intermediate 9 (a compound described in Japanese Patent Publication Open to Public Inspection No. 224369/1993, page 34), 3.0 g of p-toluenesulfonic acid and 800 ml of toluene were added. While removing produced water, the mixture was heated and refluxed for 10 hours. The resulting solution was cooled to room temperature. Following that, it was washed with a dilute sodium hydrogen carbonate aqueous solution for three time. Then, the resulting solution was further washed with water. The resulting organic phase was dried with anhydrous magnesium sulfate. Following that, toluene, used as a solvent, was distilled off under reduced pressure. Brown oily product was refined in column chromatography. After that, it was recrystalized with hexane. Thus, 42.8 g of white crystallized M-6 was obtained. (The structure thereof was confirmed by $^1$H-NMR, FD massspectral analysis and IR spectral analysis.)

It is preferable that the magenta coupler used in the present invention is incorporated in a silver halide emulsion. When incorporating, any conventional method can be employed. The magenta coupler of the present invention is dissolved in a high boiling organic solvent having a boiling point of 175° C. or higher such as tricresylphosphate and dibutylphthalate or a low boiling solvent such as ethyl acetate and butylpropionate independently or, if necessary, in a mixed solution thereof. After that, the mixture was mixed with an gelatin aqueous solution containing a surfactant. Next, after emulsifying the solution with a high speed rotary mixer or a colloid mill. Then, the resulting solution can be added to a silver halide emulsion.

The magenta coupler of the present invention can be used in a range of $1\times10^{-3}$ to 1 mol per mol of silver halide and preferably $1\times10^{-2}$ mol to $8\times10^{-1}$ mol per mol of silver halide.

The magenta coupler relating to the present invention may be used in combination with other magenta couplers.

It is further allowed to use the magenta couplers relating to the invention with an image stabilizer represented by the following Formula [A] or [B] in combination.

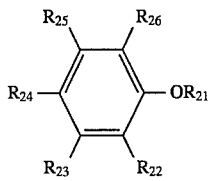

Formula [A]

wherein $R_{21}$ represents a hydrogen atom, an alkyl group, an alkenyl group, an aryl group or a heterocyclic group. Among them, the alkyl groups include, for example, the straight-chained or branched alkyl groups such as those of a methyl group, an ethyl group, a propyl group, an n-octyl group, a tert-octyl group, a benzyl group and a hexadecyl group.

The alkenyl groups represented by $R_{21}$ include, for example, an allyl group, a hexenyl group and an octenyl group.

The aryl groups represented by $R_{21}$ include, for example, a phenyl group and a naphthyl group.

The heterocyclic groups represented by $R_{21}$ include, typically, a tetrahydropyranyl group and a pyrimidyl group.

Each of the groups represented by $R_{21}$ include those having a substituent.

In Formula [A], $R_{22}$, $R_{23}$, $R_{25}$ and $R_{26}$ represent each a hydrogen atom, a halogen atom, a hydroxyl group, an alkyl group, an alkenyl group, an aryl group, an alkoxy group or an acylamino group. Among them, the alkyl, alkenyl and aryl groups include each the same alkyl, alkenyl and aryl groups described of $R_{21}$.

The above-mentioned halogen atoms include a fluorine atom, a chlorine atom and a bromine atom.

The above-mentioned alkoxy groups include, typically, a methoxy group, an ethoxy group and a benzyloxy group. Further, the acylamino group is represented by $R_{27}$—CONH— in which $R_{27}$ represents an alkyl group (such as a methyl, ethyl, n-propyl, n-butyl, n-octyl, tert-octyl or benzyl group), an alkenyl group (such as an allyl, octenyl or oleyl group), an aryl group (such as a phenyl, methoxyphenyl or naphthyl group) or a heterocyclic group (such as a pyridinyl or pyrimidyl group).

In the foregoing Formula [A], $R_{24}$ represents an alkyl group, a hydroxyl group, an aryl group, an alkoxy group, an alkenyloxy group or an aryloxy group. Among them, the alkyl and aryl groups include, typically, the same alkyl and aryl groups represented by the foregoing $R_{21}$. And, the alkoxy groups represented by $R_{24}$ include the same alkoxy groups described of the foregoing $R_{22}$, $R_{23}$, $R_{25}$ and $R_{26}$.

In addition, $R_{21}$ and $R_{22}$ may be closed in a ring so as to form a 5- or 6-membered heterocyclic ring, and $R_{23}$ and $R_{24}$ may be closed in a ring so as to form a 5-membered ring. These rings also include those spiro-bonded to other rings.

The typical examples of the compounds represented by the foregoing Formula [A] will now be given below. It is, however, to be understood that the invention shall not be limited thereto.

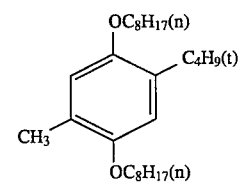

A-1

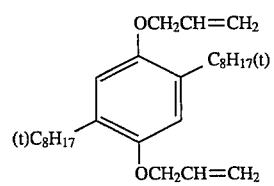

A-2

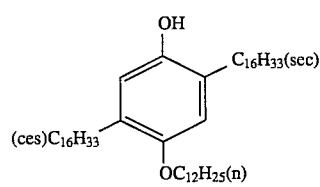

A-3

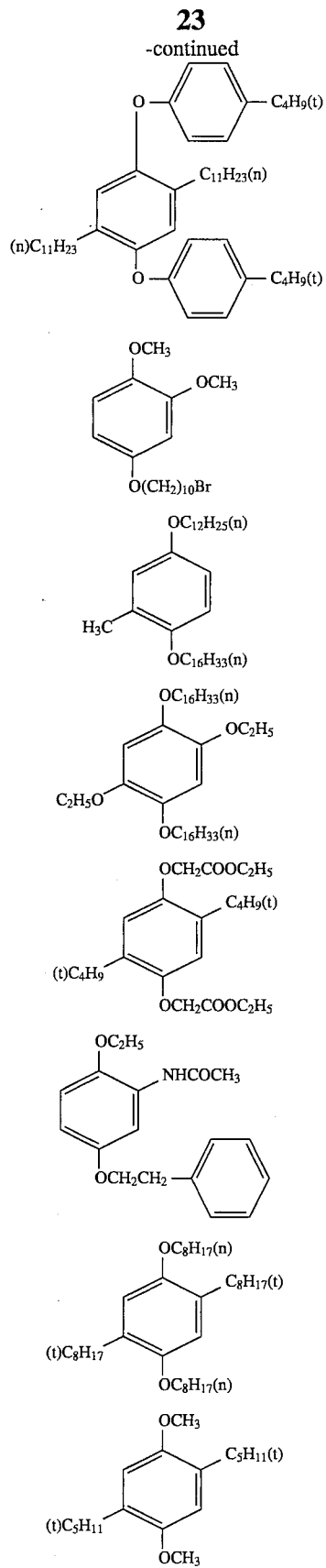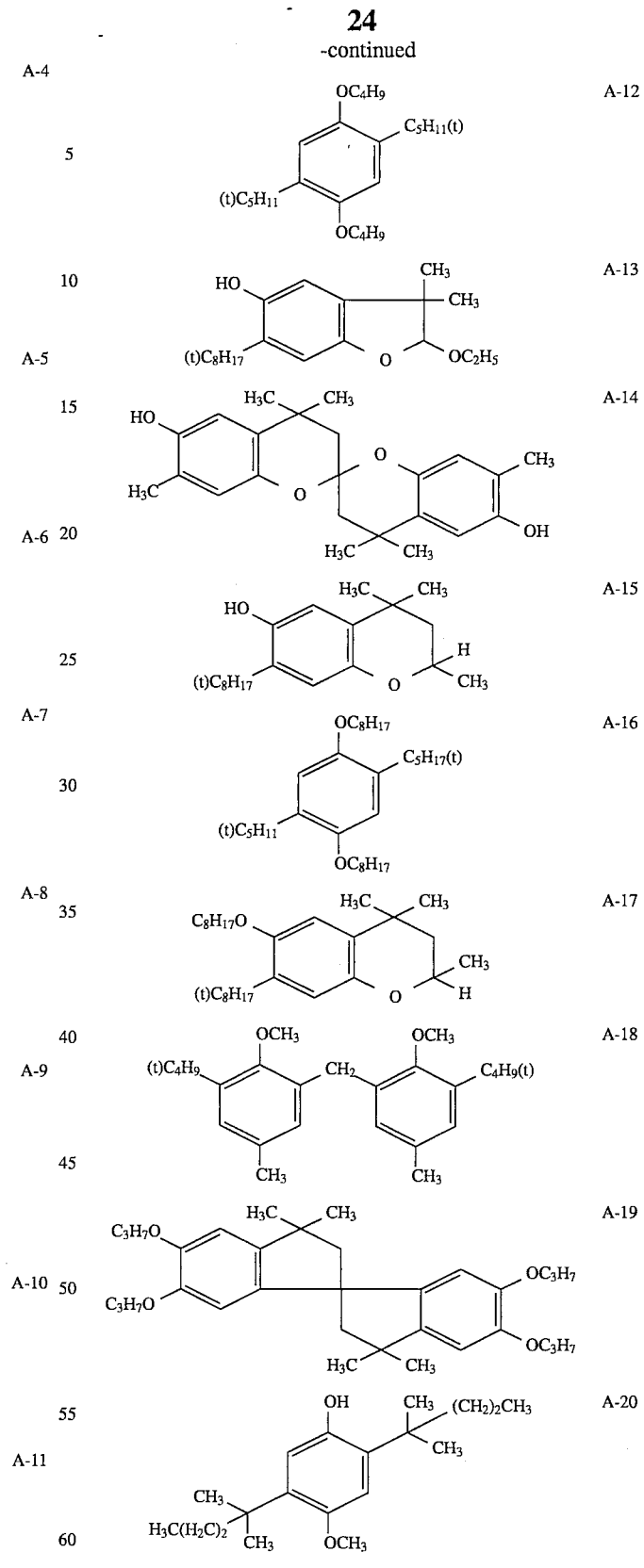

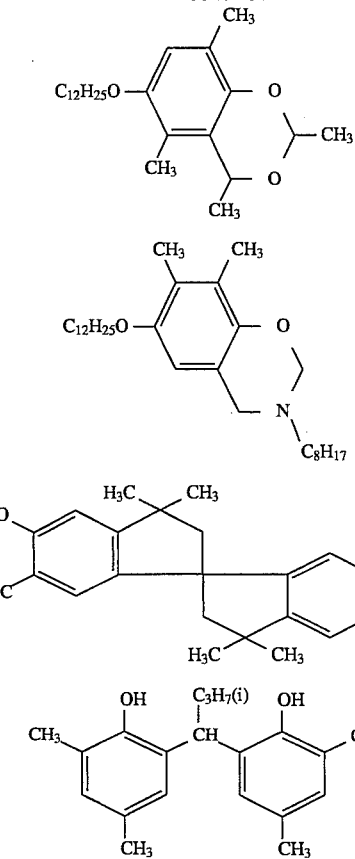

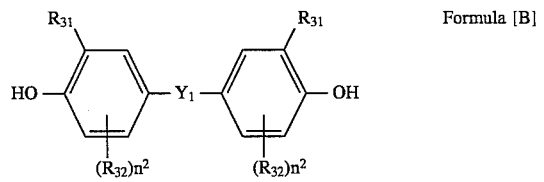

The compounds represented by Formula [A] can readily be synthesized in the procedures described in, for example, 'Journal of the Chemical Society', 1962, pp. 415–417; ibid., 1965, pp. 2904 to 2914; 'The Journal of Organic Chemistry', Vol. 23, pp. 75–76; 'Tetrahedron', Vol. 26, 1970, pp. 4743–4751; 'Chemical Letter', (4), 1972, pp. 315–316; 'Bulletin of Chemical Society of Japan' No. 10, 1972, pp. 1987–1990; and 'Bulletin of Chemical Society of Japan', Vol. 53, 1980, pp. 555–556.

Formula [B]

wherein $R_{31}$ represents a secondary or tertiary alkyl group, a secondary or tertiary alkenyl group, a cycloalkyl group or an aryl group; $R_{32}$ represents a halogen atom, an alkyl group, an alkenyl group, a cycloalkyl group or an aryl group; and $n^2$ is an integer of 0 to 3; provided, when two or more each of $R_{31}$ and $R_{33}$ are made present, they may be the same with or the different from each other.

Y represents S, SO, $SO_2$ or an alkylene group.

The secondary or tertiary alkyl groups or the secondary or tertiary alkenyl groups each represented by $R_{31}$ include desirably, those having 3 to 32 carbon atoms and, preferably, those having 4 to 12 carbon atoms. They include, typically, a t-butyl, s-butyl, t-amyl, s-amyl, t-octyl, i-propyl, i-propenyl or 2-hexenyl group.

The alkyl groups represented by $R_{32}$ include, preferably, those having 1 to 32 carbon atoms. The alkenyl groups represented by $R_{32}$ include, preferably, those having 2 to 32 carbon atoms. These groups may be straight-chained or branched and they include, typically, a methyl, ethyl, t-butyl, pentadecyl, 1-hexanonyl, 2-chlorobutyl, benzyl, 2,4-di-t-amylphenoxymethyl, 1-ethoxytridecyl, allyl or isopropenyl group.

The cycloalkyl groups represented by $R_{31}$ and $R_{32}$ include, preferably, those having 3 to 12 carbon atoms. They include, typically, a cyclohexyl, 1-methylcyclohexyl or cyclopentyl group.

The aryl groups represented by $R_{31}$ and $R_{32}$ include, preferably, a phenyl group and a naphthyl group. They include, typically, a phenyl, 4-nitrophenyl, 4-t-butylphenyl, 2,4-di-t-amylphenyl, 3-hexadecyloxyphenyl or α-naphthyl group.

The alkylene groups represented by $Y_1$ include, preferably, those having 1 to 12 carbon atoms. They include, typically, a methylene, ethylene, propylene or hexamethylene group.

Each of the groups represented by the above-mentioned $R_{31}$, $R_{32}$ and $Y_1$ are each also allowed to have a substituent.

The substituents $R_{31}$, $R_{32}$ and $Y_1$ are each allowed to have include, for example, a halogen atom and a nitro, cyano, sulfonamido, alkoxy, aryloxy, alkylthio, arylthio or acyl group.

The typical examples of the compounds represented by Formula [B] will be given below. It is, however, to be understood that the invention shall not be limited thereto.

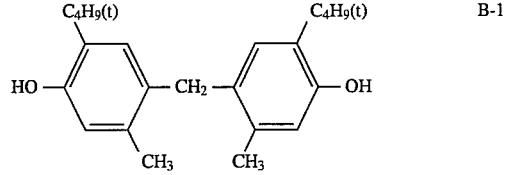

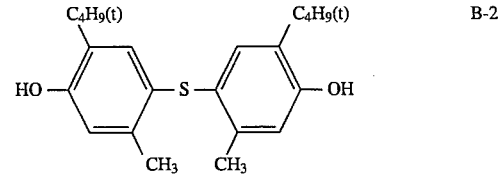

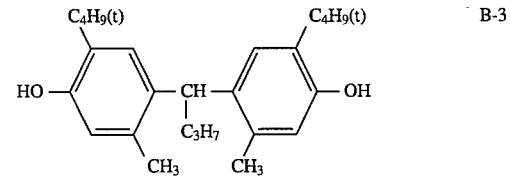

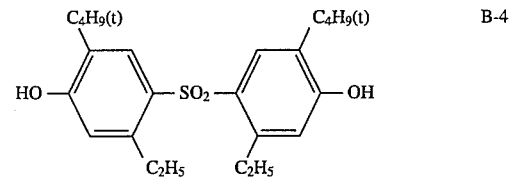

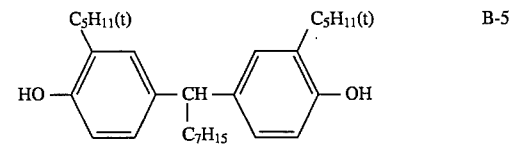

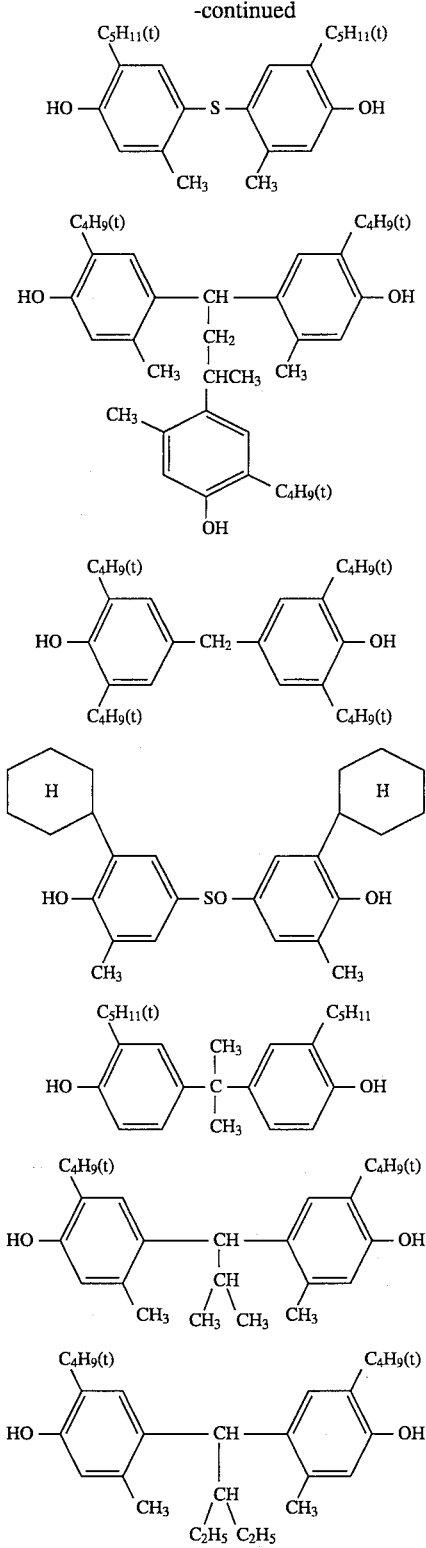

The compounds represented by Formula [B] can readily be synthesized in the procedures described in, for example, U.S. Pat. No. 2,807,653, 'Journal of the Chemical Society', Perkin I, 1979, p. 1712.

The image stabilizers represented by the foregoing Formulas [A] and [B] may be used in an amount within the range of, desirably, 5 to 400 mol % and, preferably, 10 to 250 mol % of the pyrazoloazole type magenta couplers relating to the invention.

It is preferable that the pyrazoloazole type magenta couplers of the invention and the above-mentioned image stabilizers are used in the same layer. It is, however, allowed to use the image stabilizers in the layer adjacent to a layer containing the above-mentioned couplers.

The silver halides preferably used in the invention are comprised of silver chloride, silver chlorobromide or silver chloroiodobromide and, further, they may also be comprised of a combined mixture such as the mixture of silver chloride and silver bromide.

In the silver halide emulsions applicable to the invention, it is allowed to use any one of silver halides such as silver bromide, silver iodobromide, silver iodochloride, silver chlorobromide, silver chloroiodobromide and silver chloride, provided, they can be used in ordinary silver halide emulsions.

The silver halide grains may be either those having the uniform distribution of silver halide compositions inside the grains or those of the core/shell type having the different silver halide compositions between the inside of the grains and the surface layers of the grains.

The silver halide grains may be either those capable of forming a latent image mainly on the surfaces thereof or those capable of forming a latent image mainly inside the grains thereof.

The silver halide grains may be either those having a regular crystal form such as a cube, octahedron or tetradecahedron or those having an irregular crystal form such as a globular or tabular form. It is allowed to use the grains having any ratios of {100} planes to {111} planes.

These grains may also have a mixed crystal form or may be mixed with the grains having various crystal forms.

The silver halide grains applicable there to are to have a grain size within the range of, desirably, 0.05 to 30μ and, preferably, 0.1 to 20μ.

The silver halide emulsions having any grain size distributions may be used. It is, therefore, allowed to use either the emulsions having a wide grain size distribution (hereinafter referred to as 'polydisperse type emulsions') or the independent or mixed emulsions having a narrow grain size distribution (hereinafter referred to as 'monodisperse type emulsions'). It is, further, allowed to use the mixtures of the polydisperse type and monodisperse type emulsions. The couplers applicable to the invention include a colored coupler capable of displaying a color compensation effect and the compounds capable of releasing a photographically useful fragment such as a development retarder, a development accelerator, a bleach accelerator, a developing agent, a silver halide solvent, a color toner, a layer hardener, a foggant, an antifoggant, a chemical sensitizer, a spectral sensitizer and a desensitizer. Among these compounds, it is also allowed to use the so-called DIR compounds capable of releasing a development retarder in the course of carrying out a development and improving the sharpness and graininess of an image.

The above-mentioned DIR compounds include those containing a retarder directly coupled to the coupling position thereof and those containing a retarder coupled to the coupling position through a divalent group and capable of releasing the retarder either upon intramolecular nucleophilic reaction or upon intramolecular electron-transfer reaction, produced in a group split off upon coupling reaction, (the latter compounds are hereinafter referred to as 'timing DIR compounds'). The retarders applicable thereto include those becoming diffusible upon splitting off and those not having a diffusibility so much, independently or in combination so as to meet the purposes of application.

The above-mentioned couplers are to make a coupling reaction with the oxidized products of an aromatic primary amine developing agent and these couplers may also be used in combination with a colorless coupler not forming any dyes (hereinafter referred to as 'competing coupler') as a dye-forming coupler.

The yellow couplers preferably applicable to the invention include, for example, the well-known acylacetanilide type couplers. Among these couplers, benzoyl acetanilide type and pivaloyl acetanilide type compounds may advantageously be used.

The cyan couplers preferably applicable to the invention include, for example, phenol type and naphthol type couplers.

It is also allowed to use a color-fog inhibitor for the purposes of preventing a color stain, a sharpness deterioration and/or a rough graininess, which may be produced by transferring the oxidized products of an developing agent or an electron transferrer between the emulsion layers of a light sensitive material (i.e., between the same color-sensitive layers and/or between the different color-sensitive layers).

An image stabilizer capable of preventing the deterioration of a dye image may be applied to the light sensitive materials of the invention. The compounds preferably applicable thereto are described in, for example, RD 17643, Article VII-J.

For the purposes of preventing any fog from being produced by a electric discharge generated by frictionally static-charging a light sensitive material and preventing an image from being deteriorated by UV rays, a UV absorbent may also be contained in the hydrophilic colloidal layers thereof such as the protective layers and interlayers.

For the purpose of preventing a magenta-dye forming coupler from being deteriorated by formalin in the course of preserving a light sensitive material, a formalin scavenger may further be used in the light sensitive material.

The invention can preferably be applied to a color negative film, a color paper, a color reversal film and so forth.

Now, the invention will be detailed with reference to the following preferred embodiments. It is, however, to be understood that the embodiments of the invention shall not be limited thereto.

EXAMPLE 1

Sample 101 of multilayered silver halide color photographic light sensitive materials was prepared in the following manner. Over to a polyethylene-laminated paper support containing polyethylene on one side thereof and titanium oxide on the other side thereof, each of the layers having the compositions shown in the following Tables 1 and 2 were coated thereover on the side of the polyethylene layer containing titanium oxide.

TABLE 1

| Layer | Composition | Amount added (g/m$^2$) |
|---|---|---|
| 7th layer (Protective layer) | Gelatin | 1.00 |
| 6th layer (UV abosrbing layer) | Gelatin | 0.40 |
| | UV absorbent (UV-1) | 0.10 |

TABLE 1-continued

| Layer | Composition | Amount added (g/m$^2$) |
|---|---|---|
| | UV absorbent (UV-2) | 0.04 |
| | UV absorbent (UV-3) | 0.16 |
| | Antistaining agent (HQ-1) | 0.01 |
| | DNP | 0.20 |
| | PVP | 0.03 |
| | Anti-irradiation dye (AIC-1) | 0.02 |
| 5th layer (Res-sensitive layer) | Gelatin | 1.30 |
| | Red-sensitive silver chlorobromide emulsion (Em-R) | 0.21 |
| | Cyan coupler (EC-1) | 0.24 |
| | Cyan coupler (EC-2) | 0.08 |
| | Dye-image stabilizer (ST-1) | 0.20 |
| | Antistaining agent (HQ-1) | 0.01 |
| | HBS-1 | 0.20 |
| | DOP | 0.20 |
| 4th layer (UV absorbing layer) | Gelatin | 0.94 |
| | UV absorbent (UV-1) | 0.28 |
| | UV absorbent (UV-2) | 0.09 |
| | UV absorbent (UV-3) | 0.38 |
| | Antistaining agent (HQ-1) | 0.03 |
| | DNP | 0.40 |
| 3rd layer (Green-sensitive layer) | Gelatin | 1.40 |
| | Green-sensitive silver chlorobromide emulsion (Em-G) | 0.17 |
| | Magenta coupler (EM-1) | 0.75* |
| | DNP | 0.20 |
| | Dye-image stabilizer (ST-3) | 0.75* |
| | Anti-irradiation dye (AIM-1) | 0.01 |
| 2nd layer (Interlayer) | Gelatin | 1.20 |
| | Antistaining agent (HQ-2) | 0.03 |
| | Antistaining agent (HQ-3) | 0.03 |
| | Antistaining agent (HQ-4) | 0.05 |
| | Antistaining agent (HQ-5) | 0.23 |
| | DIDP | 0.06 |
| | Antimold (F-1) | 0.002 |

TABLE 2

| Layer | Composition | Amount added (g/m$^2$) |
|---|---|---|
| 1st layer (Blue-sensitive layer) | Gelatin | 1.20 |
| | Blue-sensitive silver chlorobromide emulsion (Em-B) | 0.26 |
| | Yellow coupler (EY-1) | 0.80 |
| | Dye-image stabilizer (ST-1) | 0.30 |
| | Dye-image stabilizer (ST-2) | 0.20 |
| | Antistaining agent (HQ-1) | 0.02 |
| | Anti-irradiation dye (AIY-1) | 0.01 |
| | DNP | 0.20 |
| Support | Polyethylene-laminated paper sheet | |

*milli-mol/m$^2$
Amounts of the silver halide emulsions added were each shown in terms of the silver contents.

The coating solutions were each prepared in the following manner.

Coating solution for the 1st layer

Ethyl acetate of 60 cc was added and dissolved into 26.7 g of yellow coupler (EY-1), 10.0 g of dye-image stabilizer (ST-1), 6.67 g of a dye-image stabilizer (ST-2), 0.67 g of antistaining agent (HQ-1) and 6.67 g of high-boiling organic solvent (DNP). The resulting solution was emulsified and dispersed in 220 cc of an aqueous 10% gelatin solution containing 7 cc of an aqueous 20% surfactant (SU-2) solution by making use of a supersonic homogenizer, so that a yellow coupler dispersed solution could be prepared.

The resulting dispersed solution was mixed with the following blue-sensitive silver halide emulsion (containing 8.67 g of silver) and antiirradiation dye (AIY-1) was further added thereto, so that the coating solution for the 1st layer could be prepared.

The coating solutions for the 2nd through 7th layers were also prepared in the same manner as in the above-mentioned coating solution for the 1st layer. Besides, for the layer hardeners, (HH-1) were each added to the 2nd and 4th layers and (HH-2) to the 7th layer, respectively. For the coating aids, surfactants (SU-1) and (SU-3) were each added thereto so that the surface tension of each layer could be controlled.

The chemical structures of the compounds applied to each of the above-mentioned layers were as follows.

EY-1
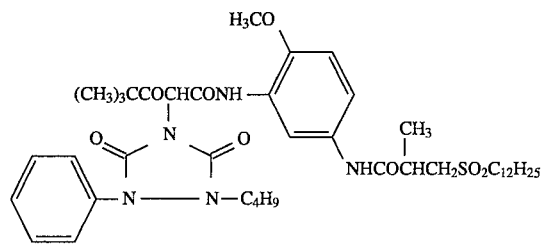

EC-1
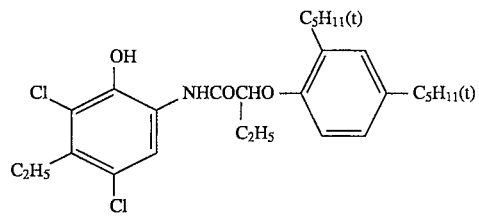

EC-2
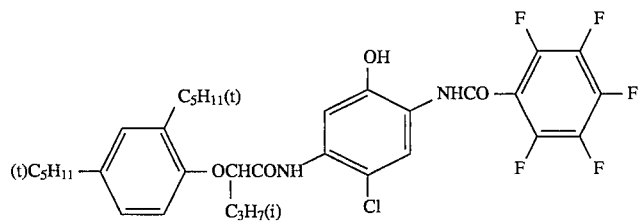

ST-1
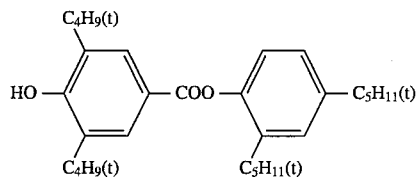

ST-2
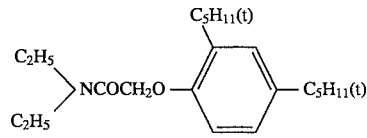

ST-3
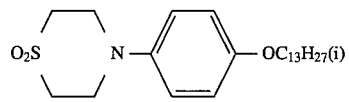

EM-1
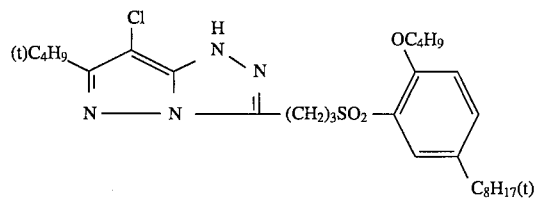

EM-2
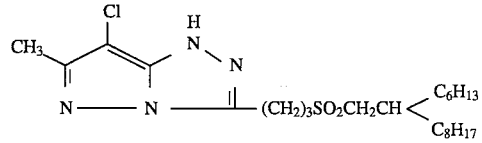

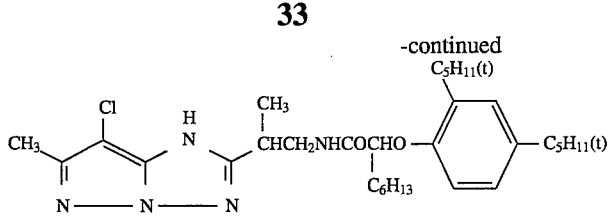
EM-3
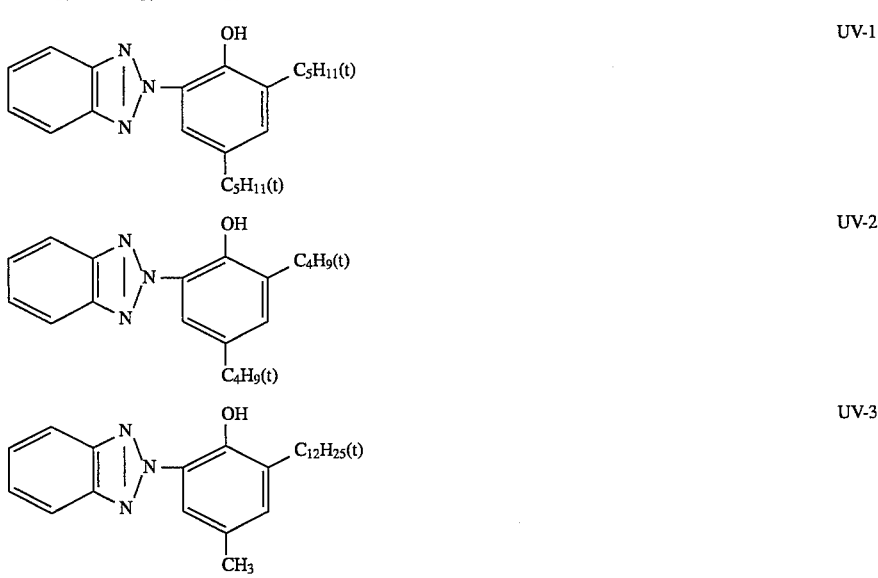
UV-1
UV-2
UV-3
DOP = Dioctyl phthalate
DNP = Dinonyl phthalate
DIDP = Diisodecyl phthalate
PVP = Polyvinyl pyrrolidone
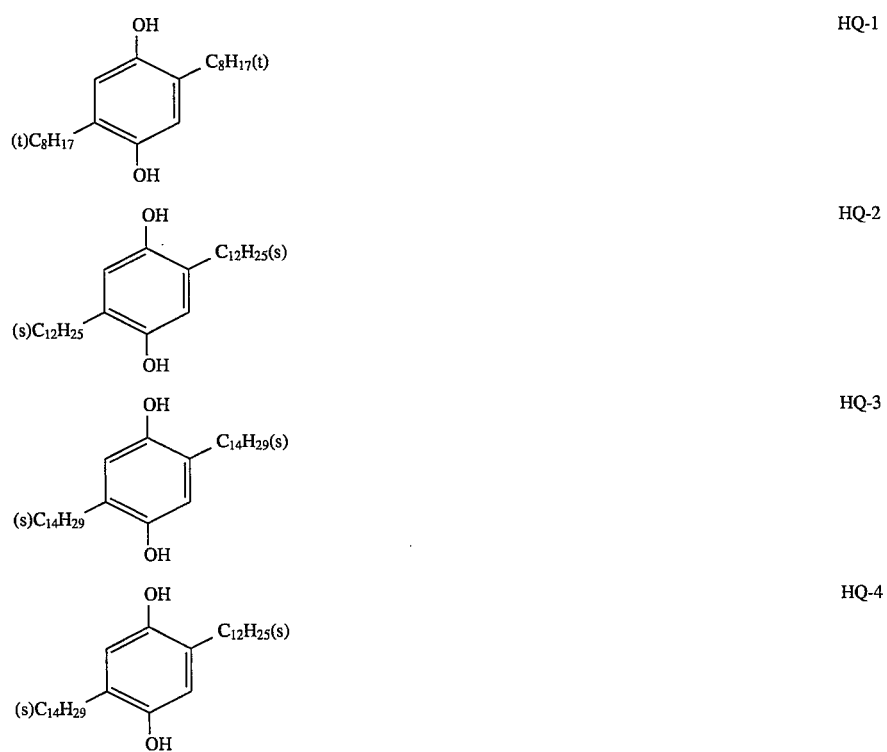
HQ-1
HQ-2
HQ-3
HQ-4

-continued
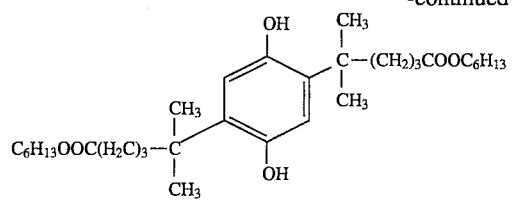  HQ-5
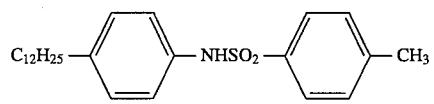  HBS-1
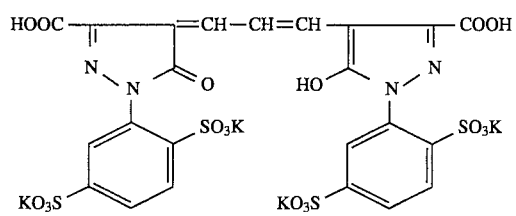  AIM-1
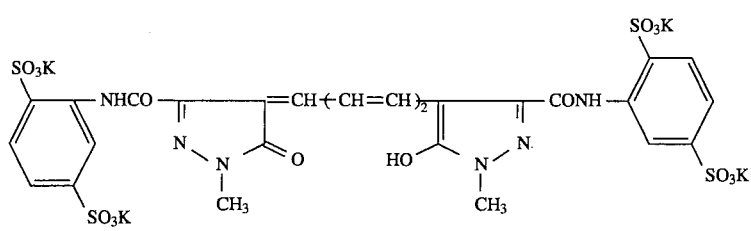  AIC-1
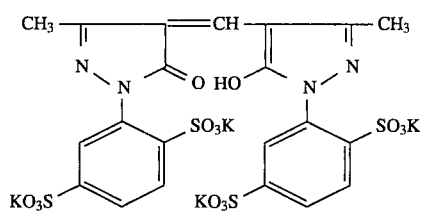  AIY-1
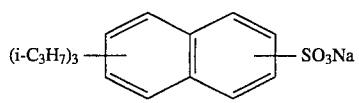  SU-1
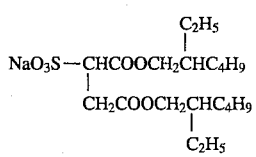  SU-2
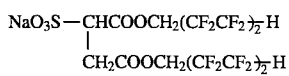  SU-3
$C(CH_2SO_2CH=CH_2)_4$  HH-1
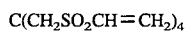
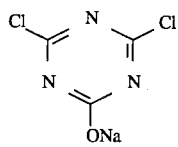  HH-2
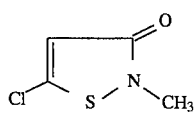  F-1

Blue-sensitive Silver Halide Emulsion (Em-B)

This was a monodisperse type cubic silver chlorobromide emulsion having an average grain size of 0.85 µm, a variation coefficient of 0.07 and a silver chloride content of 99.5 mol %.

| Sodium thiosulfate | 0.8 mg/mol of AgX |
|---|---|
| Chloroauric acid | 0.5 mg/mol of AgX |
| Stabilizer STAB-1 | $6 \times 10^{-4}$ mols/mol of AgX |
| Sensitizing dye BS-1 | $4 \times 10^{-4}$ mols/mol of AgX |
| Sensitizing dye BS-2 | $1 \times 10^{-4}$ mols/mol of AgX |

Red-sensitive Silver Halide Emulsion (Em-R)

This was a monodisperse type cubic silver chlorobromide emulsion having an average grain size of 0.50 µm, a variation coefficient of 0.08 and a silver chloride content of 99.5 mol %.

| Sodium thiosulfate | 1.8 mg/mol of AgX |
|---|---|
| Chloroauric acid | 2.0 mg/mol of AgX |
| Stabilizer STAB-1 | $6 \times 10^{-4}$ mols/mol of AgX |
| Sensitizing dye RS-1 | $1 \times 10^{-4}$ mols/mol of AgX |

The chemical structures of the compounds applied to each of the monodiserse type cubic emulsions were as follows.

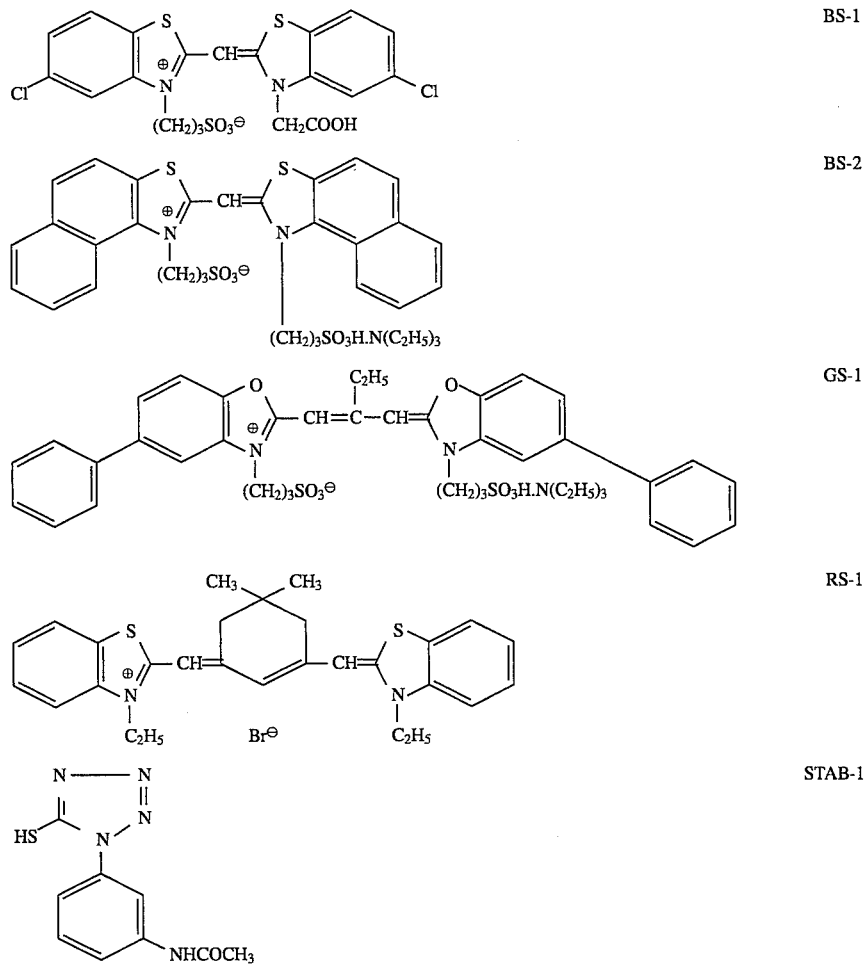

Green-sensitive Silver Halide Emulsion (Em-G)

This was a monodisperse type cubic silver chlorobromide emulsion having an average grain size of 0.43 µm, a variation coefficient of 0.08 and a silver chloride content of 99.5 mol %.

| Sodium thiosulfate | 1.5 mg/mol of AgX |
|---|---|
| Chloroauric acid | 1.0 mg/mol of AgX |
| Stabilizer STAB-1 | $6 \times 10^{-4}$ mols/mol of AgX |
| Sensitizing dye GS-1 | $4 \times 10^{-4}$ mols/mol of AgX |

Next, Samples 102 through 107 were each prepared in the same manner as in Sample 101, except that the coupler EM-1 of the 3rd layer was replaced by the same mols of the coupler of the invention shown in the following Table-3 and the dye-image stabilizer was replaced by those shown in Table-3, respectively.

The resulting samples were each exposed to green light through a wedge in an ordinary procedures and they were then processed in the following processing steps.

| Processing step | Temperature | Time |
| --- | --- | --- |
| Color developing | 35.0 ± 0.3° C. | 45 sec |
| Bleach-fixing | 35.0 ± 0.5° C. | 45 sec |
| Stabilizing | 30 to 34° C. | 90 sec |
| Drying | 60 to 80° C. | 60 sec |

The compositions of each of the processing solution will be given below.

The processing solutions were each replenished in an amount of 80 cc per m² of a subject silver halide color photographic light sensitive material.

| Color developer | Tank solution | Replenishing solution |
| --- | --- | --- |
| Pure water | 800 cc | 800 cc |
| Triethanol amine | 10 g | 18 g |
| N,N-diethyl hydroxyl amine | 5 g | 9 g |
| Potassium chloride | 2.4 g | |
| 1hydroxyethylidene-1,1-diphosphoric acid | 1.0 g | 1.8 g |
| N-ethyl-N-β-methanesulfonamidoethyl-3-methyl-4-aminoaniline sulfate | 5.4 g | 8.2 g |
| Fluorescent whitening agent, (a 4,4'-diaminostilbene sulfonic acid derivative) | 1.0 g | 1.8 g |
| Potassium carbonate | 27 g | 27 g |

Add water to make in total of 1000 cc

Adjust pH values of the tank solution to be 10.0 and of the replenisher to be 10.60, respectively.

| Bleach-fixer (The same in both of the tank solution and the replenishing solution) | |
| --- | --- |
| Ferric ammonium ethylenediamine tetraacetate, dehydrate | 60 g |
| Ethylenediaminetetraacetic acid | 3 g |
| Ammonium thiosulfate (in an aqueous 70% solution) | 100 cc |
| Ammonium sulfite (in an aqueous 40% solution) | 27.5 cc |
| Add water to make in total of | 1000 cc |
| Adjust pH with potassium carbonate or glacial acetic acid to be | pH 5.7 |

| Stabilizer (The same in both of the tank solution and the replenisher) | |
| --- | --- |
| 5-chloro-2-methyl-4-isothiazoline-3-one | 1.0 g |
| Ethylene glycol | 1.0 g |
| 1-hydroxyethylidene-1,1-diphosphonic acid | 2.0 g |
| Ethylenediaminetetraacetic acid | 1.0 g |
| Ammonium hydroxide (in an aqueous 20% solution) | 3.0 g |
| Fluorescent whitening agent (a 4,4'-diaminostilbene sulfonic acid derivative) | 1.5 g |
| Add water to make in total of | 1000 cc |
| Adjust pH with sulfuric acid or potassium hydroxide to be | pH 7.0 |

The following evaluation were each carried out by making use of the samples which were continuously processed.

<Dmax>

The maximum color densities thereof were measured.

<Light-fastness>

The resulting samples were each exposed to a xenon (fadometer) for 7 days and the dye image residual percentage (%) thereof at the initial density of 1.0 were found out.

The results thereof are shown in Table 3.

TABLE 3

| Sample No. | Magenta coupler in the third layer | Image stabilizer | Dmax | Light-fastness residual ratio (%) |
| --- | --- | --- | --- | --- |
| 101 (Comp) | EM-1 | ST-3 | 1.96 | 76 |
| 102 (Inv) | M-6 | not added | 2.36 | 94 |
| 103 (Inv) | M-8 | not added | 2.40 | 94 |
| 104 (Inv) | M-9 | not added | 2.31 | 91 |
| 105 (Inv) | M-11 | not added | 2.24 | 90 |
| 106 (Inv) | M-12 | not added | 2.26 | 88 |
| 107 (Inv) | M-19 | not added | 2.24 | 80 |

As is apparent from Table 3, when comparing Samples 102 through 107 (inventive Samples) each employing the magenta coupler of the present invention to Sample 101, it was proved that the inventive samples were remarkably improved in light-fastness and Dmax.

EXAMPLE 2

Samples 121 through 125 wherein the magenta coupler in the 3rd layer of Sample 101 of Example 1 was replaced with the coupler having equivalent mol as shown in the following Table 4 were prepared.

The resulting samples were subjected to the same evaluation as in Example 1. Table 4 shows the results thereof.

TABLE 4

| Sample No. | Magenta coupler in the third layer | Image stabilizer | Dmax | Light-fastness residual ratio (%) |
| --- | --- | --- | --- | --- |
| 121 (Comp) | EM-2 | ST-3 | 2.42 | 33 |
| 122 (Inv) | M-1 | not added | 2.50 | 60 |
| 123 (Inv) | M-14 | not added | 2.43 | 51 |
| 124 (Inv) | M-16 | not added | 2.57 | 81 |
| 125 (Inv) | M-20 | not added | 2.55 | 82 |

As is apparent from Table 4, samples 122 through 125 (inventive Samples) each using the magenta coupler of the present invention show improved results in Dmax and light-fastness compared to comparative sample 121 (comparative).

EXAMPLE 3

Samples 131 through 134 wherein the magenta coupler in the 3rd layer of Sample 101 of Example 1 was replaced with the coupler having the equivalent mol as shown in Table 5 mentioned below were prepared.

The resulting samples were evaluated by the same methods as in Example 1. Table 5 shows the results thereof.

TABLE 5

| Sample No. | Magenta coupler in the third layer | Image stabilizer | Dmax | Light-fastness residual ratio (%) |
| --- | --- | --- | --- | --- |
| 131 (Comp) | EM-3 | ST-3 | 1.75 | 70 |
| 132 (Inv) | M-21 | not added | 2.04 | 91 |
| 133 (Inv) | M-23 | not added | 2.00 | 90 |
| 134 (Inv) | M-24 | not added | 1.96 | 91 |

As is apparent from Table 5, when comparing Samples 132 through 134 (inventive Samples) each using the magenta coupler of the present invention to comparative Sample 131, it was proved that the inventive samples were remarkably improved in light-fastness and Dmax.

EXAMPLE 4

Reflective spectral absorption spectral of Samples 101 through 107 in Example 1 was measured. λmax and $\Delta\lambda_{L0.2}$ were measured. Table 6 shows the results thereof.

λmax; Maximum absorption wavelength of wedge at the reflection optical density at 1.0.

$\Delta\lambda_{L0.2}$ represents difference between wavelength at the longer wavelength side compared to the maximum absorption wavelength giving the degree of absorption of 0.2 at a wedge having reflection optical density at 1.0 and the maximum wavelength (the degree of absorption of λmax is defined to be 1.0. The smaller this value is, the more the absorption is sharp.)

TABLE 6

| Sample No. | Magenta coupler in the third layer | Image stabilizer | λmax | $\Delta\lambda_{L0.2}$ (nm) |
| --- | --- | --- | --- | --- |
| 101 (Comp) | EM-1 | ST-3 | 547 | 81 |
| 102 (Inv) | M-6 | not added | 549 | 67 |
| 103 (Inv) | M-8 | not added | 548 | 65 |
| 104 (Inv) | M-9 | not added | 549 | 71 |
| 105 (Inv) | M-11 | not added | 547 | 72 |
| 106 (Inv) | M-12 | not added | 548 | 72 |
| 107 (Inv) | M-19 | not added | 546 | 76 |

As is apparent from Table 6, sample 102 through 107 each using the magenta coupler of the present invention show sults the reduction of $\Delta\lambda_{L0.2}$ (the absorption has become sharp) compared to Sample 101 using comparative coupler. As a result, color reproducibility of samples 102 through 107 has been improved.

What is claimed is:

1. A silver halide color photographic light-sensitive material comprising a support having provided thereon at least one green-sensitive silver halide emulsion layer containing a magenta coupler represented by Formulas I or II:

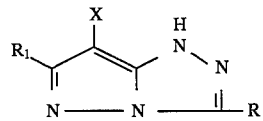

Formula I

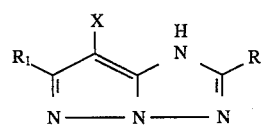

Formula II wherein $R_1$ represents a substituent; X represents a hydrogen atom or a group capable of splitting off upon reaction with an oxidized product of a color developing agent; and R represents a substituted alkyl group containing at least two units represented by Formula IV:

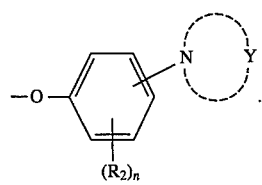

Formula IV

2. The silver halide color photographic light-sensitive material of claim 1, wherein said $R_1$ of said Formula I or said Formula II is an alkyl group having 1 to 32 carbon atoms, and said non-metallic atomic group represented by said Y comprises >O group or

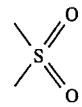

group.

3. The silver halide color photographic light-sensitive material of claim 1, wherein said magenta coupler is represented by Formula I:

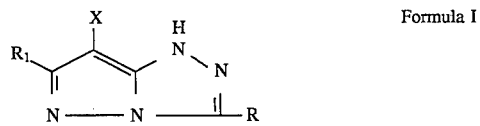

Formula I wherein $R_1$ represents a substituent; X represents a hydrogen atom or a group capable of splitting off upon reaction with an oxidized product of a color developing agent; and R represents a substituted alkyl group containing at least two units represented by Formula IV:

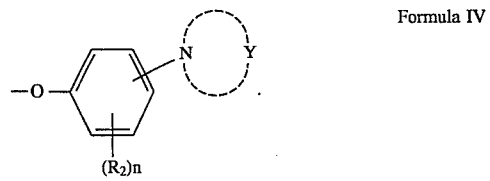

Formula IV

4. The silver halide color photographic light-sensitive material of claim 1, wherein said magenta coupler is represented by Formula II:

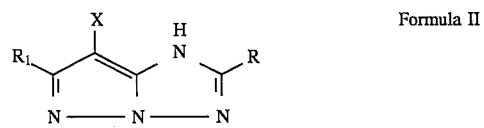

Formula II wherein $R_1$ represents a substituent; X represents a hydrogen atom or a group capable of splitting off upon reaction with an oxidized product of a color developing agent; and R represents a substituted alkyl group containing at least two units represented by Formula IV:

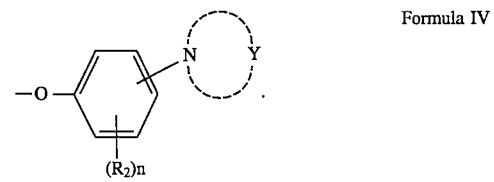

Formula IV

5. A silver halide color photographic light-sensitive material comprises a support having provided thereon at least one green-sensitive silver halide emulsion layer containing a magenta coupler represented by Formulas I-c or II-c:

Formula I-c

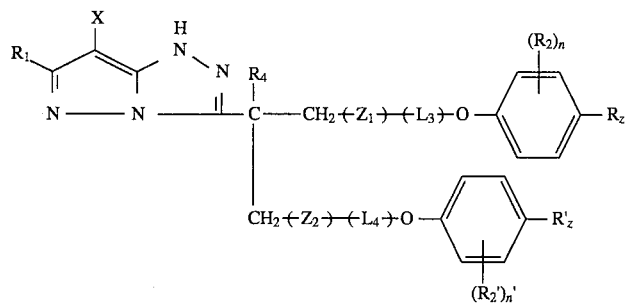

Formula II-c

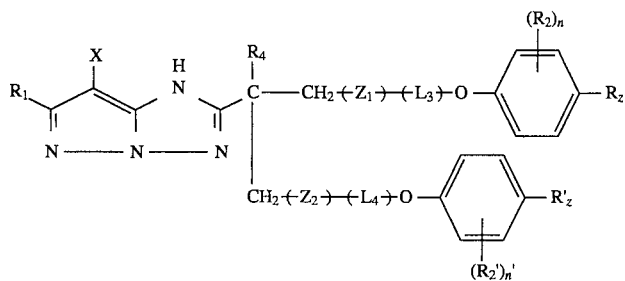

wherein $R_1$ represents an alkyl group having 1 to 4 carbon atoms; X represents a hydrogen atom or a group capable of splitting off upon reaction with an oxidized product of a color developing agent; $R_2$ and $R_2'$ each represent a substituent; $R_4$ represents a hydrogen atom, a substituted or unsubstituted alkyl group; $Z_1$ and $Z_2$ each represent

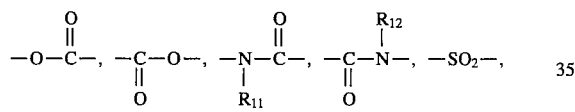

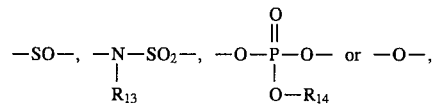

$R_{11}$, $R_{12}$, $R_{13}$ and $R_{14}$ each represent a hydrogen atom or a substituent; $L_3$ and $L_4$ each represent an alkylene group; n and n' represent an integer of 0 to 4; $R_z$ and $R'_z$ each represents

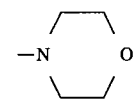

group or

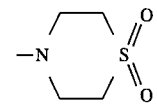

group.

6. A silver halide color photographic light-sensitive material comprising a support having provided thereon at least one green-sensitive silver halide emulsion layer containing a magenta coupler represented by Formulas I-a or II-a:

Formula I-a

-continued

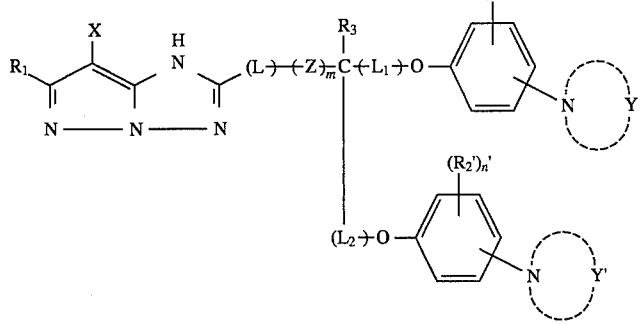

Formula II-a wherein $R_1$ represents a substituent; X represents a hydrogen atom or a group capable of splitting off upon reaction with an oxidized product of a color developing agent; $R_2$ and $R_2'$ represent a substituent; $R_3$ represents a hydrogen atom or a substituent; L represents a single linkage or a divalent linkage group; Z represents

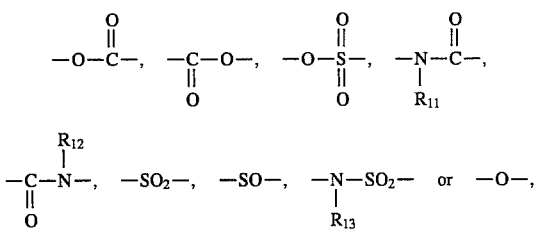

m represents 0 or 1; $R_{11}$, $R_{12}$, and $R_{13}$, each represent a hydrogen atom or a substituent; $L_1$ and $L_2$ represent a divalent linkage group; n and n' each represent an integer of 0 to 4; Y and Y' each represent a non-metal atomic group necessary to form a 5-membered or 6-membered heterocyclic ring together with a nitrogen atom, provided that m represents 0 when L represents a single linkage.

7. The silver halide color photographic light-sensitive material of claim 6, wherein said $R_1$ of said Formula I or said Formula II is an alkyl group having 1 to 32 carbon atoms, and said non-metallic atomic group represented by said Y or said >O group or

group.

8. A silver halide color photographic light-sensitive material comprising a support having provided thereon at least one green-sensitive silver halide emulsion layer containing a magenta coupler represented by Formulas I-b or II-b:

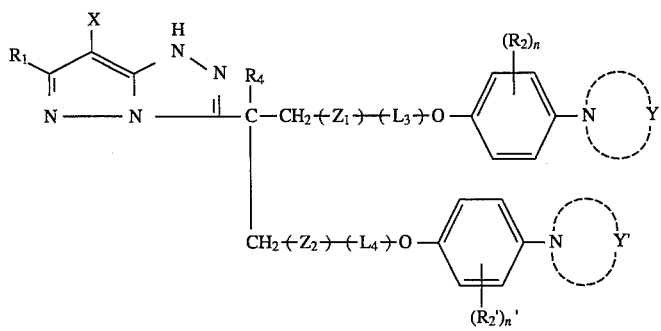

Formula I-b

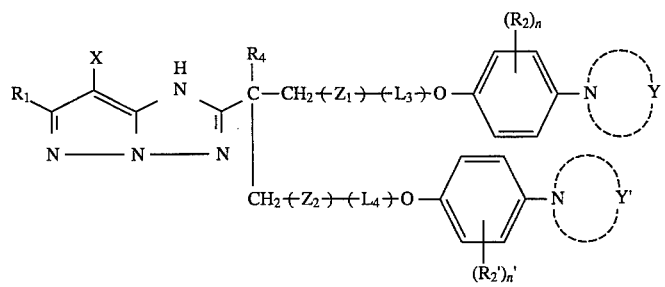

Formula II-b wherein $R_1$ represents a substituent; X represents a hydrogen atom or a group capable of splitting off upon reaction with an oxidized product of a color developing agent; $R_2$ and $R_2'$ each represent a substiment; $R_4$ represents a hydrogen atom, a substituted or unsubstimted alkyl group; $Z_1$ and $Z_2$ each represent

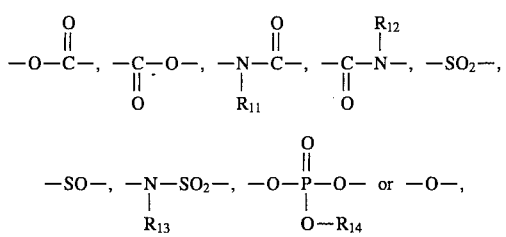

$R_{11}$, $R_{12}$, $R_{13}$, and $R_{14}$ each represent a hydrogen atom or a substituent; $L_3$ and $L_4$ each represent an alkylene group; n and n' represent an integer of 0 to 4; Y and Y' each represent a non-metal atomic group necessary to form a 5-membered or 6-membered heterocyclic ring together with a nitrogen atom.

9. The silver halide color photographic light-sensitive material of claim 8, wherein said $R_1$ of said Formula I-b or said Formula II-b is an alkyl group having 1 to 32 carbon atoms, and said non-metallic atomic group represented by said Y or said Y' comprises
>O group or

group.

* * * * *

UNITED STATES PATENT AND TRADEMARK OFFICE
CERTIFICATE OF CORRECTION

PATENT NO. : 5,492,798
DATED : February 20, 1996
INVENTOR(S) : Hiroshi KITA et al.

It is certified that error appears in the above-indentified patent and that said Letters Patent is hereby corrected as shown below:

Claim 2, column 42, lines 1-4 are wrong size type;
Claim 2, column 42, line 2, "wherein" should be indented;
line 3 should be double indented;
line 4 should be double indented;
line 4, after "comprises" should be a new double indented line;
line 4, ">0 group" should read
-- $\searrow\!\!\!\!\nearrow$O group--.

Claim 7, column 46, line 17, after "said" start new line.
line 17, ">0 group" should read
-- Y' comprises $\searrow\!\!\!\!\nearrow$O group--.

Claim 8, column 46, line 65, "substiment" should read
--substituent--;
line 67 "stimted" should read
--stituted--.

Claim 9, column 48, line 8, ">0" should read
-- $\searrow\!\!\!\!\nearrow$O --

Signed and Sealed this

Eleventh Day of February, 1997

Attest:

BRUCE LEHMAN

Attesting Officer

Commissioner of Patents and Trademarks